(12) United States Patent
Bartsch et al.

(10) Patent No.: US 9,546,198 B2
(45) Date of Patent: Jan. 17, 2017

(54) CYCLIC PEPTIDES AS ADAM PROTEASE INHIBITORS

(71) Applicant: King's College London, London (GB)

(72) Inventors: Joerg Bartsch, London (GB); Garrit Koller, London (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 14/798,825

(22) Filed: Jul. 14, 2015

(65) Prior Publication Data

US 2016/0168202 A1 Jun. 16, 2016

Related U.S. Application Data

(63) Continuation of application No. 12/682,482, filed as application No. PCT/GB2008/003441 on Oct. 10, 2008, now abandoned.

(30) Foreign Application Priority Data

Oct. 12, 2007 (GB) .................................. 0719997.9

(51) Int. Cl.
C07K 4/00 (2006.01)
C07K 5/00 (2006.01)
(Continued)

(52) U.S. Cl.
CPC .............. C07K 7/64 (2013.01); A61K 38/005 (2013.01); A61K 38/12 (2013.01); C07K 5/0202 (2013.01); C07K 5/12 (2013.01); C07K 5/123 (2013.01); C07K 5/126 (2013.01); C07K 7/56 (2013.01); C07K 14/8146 (2013.01); C12N 9/6489 (2013.01); A61K 38/00 (2013.01)

(58) Field of Classification Search
None
See application file for complete search history.

(56) References Cited

U.S. PATENT DOCUMENTS 5,565,332 A 10/1996 Hoogenboom et al.
5,879,657 A 3/1999 DeGrado et al.
(Continued)

FOREIGN PATENT DOCUMENTS

EP 0552417 A1 7/1993
EP 0584421 A1 3/1994
(Continued)

OTHER PUBLICATIONS

Strijowski, [Synthesis and Conformational Analysis of Cyclic Peptides as Potential Ligands of Integrins], Doctorate Dissertation, Chapter 4.4, pp. 109-114, Tables 12-14 (2004). English translation of Tables 12-14 only.

(Continued)

*Primary Examiner* — Kevin S Orwig
(74) *Attorney, Agent, or Firm* — Marshall, Gerstein & Borun LLP

(57) ABSTRACT

The invention relates to a method for inhibiting an ADAM protease, comprising inhibiting binding to an integrin-binding loop of a disintegrin domain in the ADAM protease. Also provided are cyclic peptides which inhibit binding to an integrin-binding loop of an ADAM protease, as well as associated pharmaceutical compositions, uses and methods of treatment.

16 Claims, 8 Drawing Sheets

(51) Int. Cl.

| C07K 5/12 | (2006.01) |
| C07K 7/64 | (2006.01) |
| A61K 38/03 | (2006.01) |
| A61K 38/12 | (2006.01) |
| A61K 38/00 | (2006.01) |
| C07K 5/02 | (2006.01) |
| C07K 7/56 | (2006.01) |
| C07K 14/81 | (2006.01) |
| C12N 9/64 | (2006.01) |

(56) References Cited

U.S. PATENT DOCUMENTS

| 5,976,551 | A | 11/1999 | Mottez et al. |
| 6,060,585 | A | 5/2000 | Gellman et al. |
| 6,818,418 | B1 | 11/2004 | Lipovsek et al. |
| 7,589,170 | B1 | 9/2009 | Smythe et al. |
| 2003/0113764 | A1 | 6/2003 | Bodary et al. |
| 2005/0112118 | A1 | 5/2005 | Cimbora et al. |
| 2005/0203025 | A1 | 9/2005 | Blaschuk et al. |
| 2005/0260697 | A1 | 11/2005 | Wang et al. |

FOREIGN PATENT DOCUMENTS

| EP | 0616812 A1 | 9/1994 |
| EP | 1142910 A1 | 10/2001 |
| WO | WO-91/02078 A1 | 2/1991 |
| WO | WO-95/00544 A1 | 1/1995 |
| WO | WO-95/19374 A1 | 7/1995 |
| WO | WO-95/28426 A2 | 10/1995 |
| WO | WO-97/35538 A2 | 10/1997 |
| WO | WO-97/40072 A2 | 10/1997 |
| WO | WO-98/56915 A2 | 12/1998 |
| WO | WO-99/16873 A1 | 4/1999 |
| WO | WO-00/15665 A2 | 3/2000 |
| WO | WO-00/18790 A1 | 4/2000 |
| WO | WO-00/56766 A1 | 9/2000 |
| WO | WO-00/63243 A1 | 10/2000 |
| WO | WO-01/09189 A2 | 2/2001 |
| WO | WO-01/09293 A2 | 2/2001 |
| WO | WO-01/47944 A2 | 7/2001 |
| WO | WO-01/57272 A2 | 8/2001 |
| WO | WO-01/94377 A2 | 12/2001 |
| WO | WO-02/10406 A2 | 2/2002 |
| WO | WO-02/077025 A1 | 10/2002 |
| WO | WO-03/033515 A1 | 4/2003 |
| WO | WO-2004/024089 A2 | 3/2004 |
| WO | WO-2004/041862 A2 | 5/2004 |
| WO | WO-2004/100986 A2 | 11/2004 |
| WO | WO-2005/090991 A1 | 9/2005 |
| WO | WO-2005/123993 A2 | 12/2005 |
| WO | WO-2006/014903 A2 | 2/2006 |
| WO | WO-2006/064861 A1 | 6/2006 |
| WO | WO-2006/131768 A2 | 12/2006 |
| WO | WO-2007/035843 A2 | 3/2007 |

OTHER PUBLICATIONS

Altschul et al., Basic local alignment search tool. *J. Mol. Biol.* 215: 403-10 (1997).
Altschul et al., Gapped BLAST and PSI-BLAST: a new generation of protein database search programs. *Nucl. Acids Res.* 25: 3389-402 (1997).
Amour et al., The in vitro activity of ADAM-10 is inhibited by TIMP-1 and TIMP-3. *FEBS Lett.* 473: 275-9 (2000).
Aumailley et al., Arg-Gly-Asp constrained within cyclic pentapeptides. Strong and selective inhibitors of cell adhesion to vitronectin and laminin fragment P1. *FEBS Lett.* 291: 50-4 (1991).
Barker et al., Cyclic RGD peptide analogues as antiplatelet antithrombotics. *J. Med. Chem.* 35: 2040-8 (1992).
Basler et al., Conformationally constrained beta-amino acid derivatives by intramolecular [2+2]-photocycloaddition of a tetronic acid amide and subsequent lactone ring opening. *J. Org. Chem.* 70(24): 9798-808 (2005).
Berman et al., The Protein Data Bank. *Nucl. Acids Res.* 28: 235-42 (2000).
Blobel, ADAMs: Key components in EGFR signalling and development. *Nat. Rev. Mol. Cell Biol.* 6: 32-43 (2005).
Bridges et al., Integrin alpha4beta1-dependent adhesion to ADAM 28 (MDC-L) requires an extended surface of the disintegrin domain. *Biochemistry* 42: 3734-41 (2003).
Cilengtide et al., Oncolytic angiogenesis inhibitor intregrin alphavbeta3, alphavbeta5 antagonist. *Drugs of the Future*, 25(7): 674-8 (2000).
Ellington et al., In vitro selection of RNA molecules that bind specific ligands. *Nature*, 346(6287): 818-22 (1990).
Fourie et al., Catalytic activity of ADAM8, ADAM15, and MDC-L (ADAM28) on synthetic peptide substrates and in ectodomain cleavage of CD23. *J. Biol. Chem.* 278: 30469-77 (2003).
Gademann et al., Beta-peptides: twisting and turning. *Curr. Med. Chem.* 6(10): 905-25 (1999).
Gibrat et al., Surprising similarities in structure comparison. *Curr. Opin. Struct. Biol.* 6: 377-85 (1996).
Gupta et al., Characterization of Fertilinβ-disintegrin binding specificity in sperm-egg adhesion, *Bioorg. Med. Chem.*, 8: 723-9 (2000).
Henikoff et al., Amino acid substitution matrices from protein blocks. *Proc. Nat. Acad. Sci., USA,* 89: 10915-9 (1992).
Holliger et al., "Diabodies": Small bivalent and bispecific antibody fragments. *Proc. Natl. Acad. Sci. USA,* 90: 6444-8 (1993).
Holm et al., Touring protein fold space with DALI/FSSP. *Nucl. Acids Res.* 26: 316-9 (1998).
International Search Report, PCT/GB2008/003441, European Patent Office, dated Jan. 26, 2009.
Karlin et al., Applications and statistics for multiple high-scoring segments in molecular sequences. *Proc. Natl. Acad. Sci. USA,* 90: 5873-7 (1993).
Karlin et al., Methods for assessing the statistical significance of molecular sequence features by using general scoring schemes. *Proc. Natl. Acad. Sci. USA* 87: 2264-8 (1990).
Kelly et al., Metalloprotease-Disintegrin ADAM8: expression analysis and targeted deletion in mice. *Devel. Dynamics,* 232: 221-31 (2005).
King et al., Expression and regulation of a disintegrin and metalloproteinase (ADAM) 8 in experimental asthma. *Am. J. Respir. Cell Mol. Biol.* 31(3): 257-65 (2004).
Kohler et al., Continuous cultures of fused cells secreting antibody of predefined specificity. *Nature,* 256: 495-7 (1975).
Lebowitz et al., Soluble, high-affinity dimers of T-cell receptors and class II major histocompatibility complexes: biochemical probes for analysis and modulation of immune responses. *Cell Immunol.* 192(2): 175-84 (1999).
Malesevic et al., An improved method for the solution cyclization of peptides under pseudo-high dilution conditions. *J. Biotechnol.* 112: 73-7 (2004).
Marti et al., Solid phase synthesis of b-peptides via Arndt-Eistert homologation of Fmoc-protected amino acid diazoketones. *Tetrahedron Lett.* 38: 6145-8 (1997).
Moss et al., Fluorescent substrates for the proteinases ADAM17, ADAM10, ADAM8, and ADAM12 useful for high-throughput inhibitor screening. *Anal. Biochem.* 366: 144-8 (2007).
Moss et al., Therapeutic benefits from targeting of ADAM family members. *Biochemistry,* 43: 7227-35 (2004).
Murray et al., Efficient synthesis of a beta-peptide combinatorial library with microwave irradiation. *J. Am. Chem. Soc.* 127(38): 13271-80 (2005).
Murzin et al., SCOP: a structural classification of proteins database for the investigation of sequences and structures. *J. Mol. Biol.* 247: 536-40 (1995).
Myers et al., Optimal alignments in linear space. *Comput. Appl. Biosci.* 4: 11-17 (1988).
Naus et al., Ectodomain shedding of the neural recognition molecule CHL1 by the metalloprotease-disintegrin ADAM8 promotes neurite outgrowth and suppresses neuronal cell death. *J. Biol. Chem.* 279: 16083-90 (2004).
Naus et al., Identification of novel substrates for the Metalloprotease-Disintegrin ADAM8. *Biol. Chem.* 387: 337-46 (2006).

(56) References Cited

OTHER PUBLICATIONS

Orengo et al., CATH—a hierarchic classification of protein domain structures. *Structure*, 5(8): 1093-108 (1997).
Pearson et al., Improved tools for biological sequence comparison. *Proc. Nat. Acac. Sci., USA*, 85: 2444-8 (1988).
Peschon et al., An essential role for ectodomain shedding in mammalian development. *Science*, 282(5392): 1281-4 (1998).
Rawlings et al., MEROPS: the peptidase database. *Nucl. Acids Res.* 34: D270-2 (2006).
Schlomann et al., The metalloprotease-disintegrin ADAM8: Processing by autocatalysis is required for proteolytic activity and cell adhesion. *J. Biol. Chem.*277: 48210-9 (2002).
Schlomann et al., Tumor necrosis factor (TNF) alpha induces a metalloprotease-disintegrin, ADAM8 (CD 156): Implications for neuron-glia interactions during neurodegeneration. *J. Neurosci.* 20: 7964-71 (2000).
Schomburg et al., BRENDA, the enzyme database: updates and major new developments. *Nucl. Acids Res.* 32(Database issue): D431-3 (2004).
Seals et al., The ADAMs family of metalloproteases: multidomain proteins with multiple functions. *Genes Dev.* 17: 7-30 (2003).
Sekut et al., AntiTNF-alpha agents in the treatment of inflammation. *Expert Opin. Invest. Drugs*, 7: 1825-39 (1998).
Thevenard et al., Strutural and antitumor properties of the YSNSG cyclopeptide derived from tumstatin. *Chem. Biol.* 13(12): 1307-15 (2006).
Vlatakis et al., Drug assay using antibody mimics made by molecular imprinting. *Nature* 361: 645-7 (1993).
Weisshoff et al., Mimicry of betall'-turns of proteins in cyclic pentapeptides with one and without D-amino acids. *Eur. J. Biochem.* 259(3): 776-88 (1999).
Wildeboer et al., Expression levels and activities of human Metalloproteinase-disintegrins ADAM8 and ADAM19 in primary brain tumors are associated with invasive activity. *J. Neuropath. Exp. Neurol.* 65: 516-27 (2006).
Xiong et al., Crystal structure of the extracellular segment of integrin alpha Vbeta3 in complex with an Arg-Gly-Asp ligand. *Science*, 296: 151-5 (2002).
Yoshida et al., Molecular cloning of cDNA encoding MS2 antigen, a novel cell surface antigen strongly expressed in murine monocytic lineage. *Int. Immunol.* 2: 585-591 (1990).
Yuan et al., A role for the disintegrin domain of cyritestin, a sperm surface protein belonging to the ADAM family, in mouse sperm-egg plasma membrane adhesion and fusion, *J. Cell Biol.*, 137: 105-12 (1997).
Zhao et al., Inhibitory antibodies against endopeptidase activity of human adamalysin 19. *Biochem. Biophys. Res. Commun.* 289: 288-94 (2001).
Zimmermann et al., Integrin alpha5beta1 ligands: biological evaluation and conformational analysis. *Chembiochem.* 6: 272-6 (2005).
Bourne et al., The development and application of anovel safety-catch linker for BOC-base assembly of libraries of cyclic peptides. *J. Org. Chem.* 66(23): 7706-13 (2001).
Fukami et al., Structure-activity relationships of cyclic pentapeptide endothelin A receptor antagonists. J. Med. Chem. 38(21): 4309-24 (1995).
Jeon et al., Novel function of human ADAM15 disintegrin-like domain and its derivatives in platelet aggregation. Thromb. Res. 119(5): 609-19 (2007).
Ji et al., Disrupting Skp2-cyclin A interaction with a blocking peptide induces selective cancer cell killing. Molec. Cancer Therapeuti. 6(2): 684-91 (2007).
Kamioka et al., Combinatorial synthesis of RGD model cyclic peptides utilizing a palladium-catalyzed carbonylative macrolactamization on a polymer support. J. Combin. Chem. 10(5): 681-90 (2008).
Landgraf et al., Protein interaction networks by proteome peptide scanning. Curr. Opin. Chem. Biol. 7(1): 55 (2004).
Meutermans et al., Synthesis of [alpha]-aspartyl-containing cyclic peptides. Lett. Pept. Sci. 4(2): 79-84 (1997).
Müller et al., Synthesis of cyclic RGD-peptides containing [beta]-amin acids. Lett. Pept. Sci. 4(4-6): 275-81 (1997).
Quan et al., Transfer of a protein binding epitope to a minimal designed peptide. *Biopolymers*, 47(4): 265-75 (1998).
Sorbera et al., Cilengtide—Oncolytic angiogenesis inhibitor intregrin alphavbeta3, alphavbeta5 antagonist. *Drugs of the Future*, 25(7): 674-8 (2000).
Sprengard et al., Multiple sialyl lewisx N-glycopeptides: Effective ligands for E-selectin. *Ange. Chem.* 35(3): 321-4 (1996).
Stinear et al., Reductive evolution and niche adaption inferred from the genome of Mycobacterium ulcerans, the causative agent of Buruli ulcer. Genome Res. 17(2): 192-200 (2007).
Urman et al., The constrained amino acid [beta]=Acc confers potency and selectivity to integrin ligands. Ange. Chem. 46(21): 3976-8 (2007).
Wildeboer et al., Metalloproteinase disintegrins ADAM8 and ADAM19 are highly regulated in human primary brain tumors and their expression levels and activities are associated with invasiveness. *J. Neuropath. Exp. Neurol.* 65(5): 516-27 (2006).

```
hADAM9      DAGEECDCGTPKECELDPCCE------GSTCKLKSFAECAY--GDCCKD-CRFLPGGTLC 51
hADAM28     EMGEDCDCGTSEECT-NICCD------AKTCKIKATFQCAL--GECCEK-CQFKKAGMVC 50
hADAM8      ERGEQCDCGPPEDCR-NRCCN------STTCQLAEGAQCAH--GTCCQE-CKVKPAGELC 50
hADAM15     EPGEQCDCGFLDDCV-DPCCD------SLTCQLRPGAQCASD-GPCCQN-CQLRPSGWQC 51
hADAM12     ---------------NRCCN------ATTCTLKPDAVCAH--GLCCED-CQLKPAGTAC 35
hADAM19     --------------N-NPCCN------ASNCTLRPGAECAH--GSCCHQ-CKLLAPGTLC 36
hADAM33     EAGEECDCGPGQECR-DLCCF------AHNCSLRPGAQCAH--GDCCVR-CLLKPAGALC 50
hADAM10     EQGEECDCGYSDQCK-DECCFDANQPEGRKCKLKPGKQCSPSQGPCCTAQCAFKSKSEKC 59
hADAM17     DEGEECDPGIMYLNN-DTCCN-------SDCTLKEGVQCSDRNSPCCKN-CQFETAQKKC 51
                 : **              *  :      *:  . **   *  .      * hADAM9      RGK-TSECDVPEYCNGSSQFCQPDVF- 76    (SEQ ID NO:22)
hADAM28     RPA-KDECDLPEMCNGKSGNCPDDRFQ 76    (SEQ ID NO:23)
hADAM8      RPK-KDMCDLEEFCDGRHPECPEDAFQ 76    (SEQ ID NO:24)
hADAM15     RPT-RGDCDLPEFCPGDSSQCPPDV-- 75    (SEQ ID NO:25)
hADAM12     RDS-SNSCDLPEFCTGASPHCPANVYL 61    (SEQ ID NO:26)
hADAM19     REQ-ARQCDLPEFCTGKSPHCPTNFYQ 62    (SEQ ID NO:27)
hADAM33     RQA-MGDCDLPEFCTGTSSHCPPDVYL 76    (SEQ ID NO:28)
hADAM10     RD--DSDCAREGICNGFTALCPASDPK 84    (SEQ ID NO:29)
hADAM17     QEAINATCKGVSYCTGNSSECPPP--- 75    (SEQ ID NO:30)
              :     *  * *    *
```

Fig. 9A

```
mADAM8      EHGEQCDCGTPQDCQ-NPCCN------ATTCQLVKGAECAS--GTCCHE-CKVKPAGEVC 50
mADAM28     EMNEDCDCGTPKECT-NKCCD------ARTCKIKAGFQCAL--GECCEK-CQLKKPGVVC 50
mADAM12     ---------------NRCCN------ATTCTLKPDAVCAH--GQCCED-CQLKPPGTAC 35
mADAM19     --------------K-NPCCN------ASNCTLKEGAECAH--GSCCHQ-CKLVAPGTQC 36
mADAM33     EAGEECDCGSGQKCP-DPCCF------AHNCSLRAGAQCAH--GDCCAR-CLLKSAGTPC 50
mADAM15     DPGEQCDCGFPDECT-DPCCD------HFTCQLRPGAQCASD-GPCCQN-CKLHPAGWLC 51
mADAM9      DPGEECDCGTAKECEVDPCCE------GSTCKLKSFAECAY--GDCCKD-CQFLPGGSMC 51
mADAM10     EQGEECDCGYSDQCK-DDCCFDANQPEGKKCKLKPGKQCSPSQGPCCTAQCAFKSKSEKC 59
mADAM17     DEGEECDPGIMYLNN-DTCCN-------SDCTLKPGVQCSDRNSPCCKN-CQFETAQKKC 51
                 : **              *  :      *:  . **   *  .      * mADAM8      RLS-KDKCDLEEFCDGRKPTCPEDAFQ 76    (SEQ ID NO:31)
mADAM28     RAA-KDECDLPEVCDGKSSHCPGDRFR 76    (SEQ ID NO:32)
mADAM12     RGS-SNSCDLPEFCTGTAPHCPANVYL 61    (SEQ ID NO:33)
mADAM19     REQ-VRQCDLPEFCTGKSPHCPTNYY- 61    (SEQ ID NO:34)
mADAM33     RPA-ATDCDLPEFCTGTSPYCPADVYL 76    (SEQ ID NO:35)
mADAM15     RPP-TDDCDLPEFCPGDSSQCPSDI-- 75    (SEQ ID NO:36)
mADAM9      RGK-TSECDVPEYCNGSSQFCPPDVF- 76    (SEQ ID NO:37)
mADAM10     RD--DSDCAKEGICNGFTALCPASDPK 84    (SEQ ID NO:38)
mADAM17     QEAINATCKGVSYCTGNSSECPPP--- 75    (SEQ ID NO:39)
              :     *  * *   **
```

Fig. 9B

CYCLIC PEPTIDES AS ADAM PROTEASE INHIBITORS

CROSS-REFERENCE TO RELATED APPLICATIONS

This application is a continuation of U.S. patent application Ser. No. 12/682,482, filed Jul. 27, 2010, which is a U.S. National Phase of PCT/GB2008/003441, filed Oct. 10, 2008, incorporated herein by reference, which claims priority to Great Britain Patent Application No. 0719997.9 filed Oct. 12, 2007.

FIELD OF THE INVENTION

The present invention relates to methods and reagents for use in the field of inhibiting proteases, in particular proteases known as ADAMs (a disintegrin and metalloprotease domain). Inhibition of ADAMs according to the invention may be desirable in various in vitro and in vivo applications, including methods for treating diseases such as cancer.

BACKGROUND OF THE INVENTION

ADAMs (a disintegrin and metalloprotease) or MDCs (metalloprotease disintegrin cysteine-rich proteins) form a family of type I transmembrane proteins. Owing to their multidomain structure consisting of pro-, metalloprotease, disintegrin-like, cystein-rich, EGF-like, transmembrane and cytoplasmic domains, ADAMs are capable of four physiological functions: cell adhesion, cell fusion, cell signalling and proteolysis.

ADAMs are implicated in physiological processes such as fertilisation, myogenesis and neurogenesis, and are also involved in a number of pathological processes by releasing cytokines and their receptors under inflammatory conditions (see for example Moss and Bartsch, 2004). To date, 40 members are known in different species (table of ADAMs on http colon-slash-slash www.people.virginia.edu/;jw7g/). Approximately half of these ADAMs contain the catalytic consensus sequence HEXXHHXXGXXHD (SEQ ID NO:1) in their metalloprotease domains and are therefore predicted to be catalytically active. Proteolysis of membrane-anchored precursor proteins is a key event in signalling cascades (Blobel, 2005) and this process has been termed ectodomain shedding (Peschon et al., 1998). A number of ADAM substrates have been defined either by their physiological role or by their cellular localisation (Seals and Courtneidge, 2003; Moss and Bartsch, 2004; Blobel, 2005). So far, no consensus sequence on the substrate side has been reported, making prediction of potential cleavage sites difficult. Rather, ADAMs recognise a structural footprint on the extracellular part of the membrane protein, and it is assumed that cleavage occurs in the juxtamembraneous regions of these membrane proteins.

One particular area of research interest is the ADAM family member ADAM8, originally identified as MS2 or CD156 on mouse macrophages (Yoshida et al., 1990). ADAM8 is expressed in several tissues, such as thymus, cartilage, bone, brain and spinal cord, during embryonic development. As embryonic development of ADAM8-deficient mice appears normal, ADAM8 does not seem to be essential for developmental processes (Kelly et al., 2005). Rather, it is more likely that ADAM8 has a specific function in cytokine response which is reflected by its distinct expression in immune cells like B-cells, leukocytes, neutrophils, macrophages, and dendritic cells. In response to inflammatory stimuli such as lipopolysaccharide (LPS) and tumour necrosis factor a (TNF-α), ADAM8 expression is upregulated in most immune cells. In addition, ADAM8 is upregulated in the central nervous system (CNS) under inflammatory conditions in activated glia cells—astrocytes and microglia—indicating its involvement in neuron-glia signalling, in particular in neuroinflammatory disorders (Schlomann et al., 2000). Similarly to glial cells, ADAM8 is expressed in neurons at low levels, and expression is induced by TNF-α, suggesting that under inflammatory conditions in the CNS, neuronal ADAM8 activity is significantly increased (Schlomann et al., 2000).

In the lung, ADAM8 is upregulated under experimental induction of allergic asthma by inflammatory cytokines (King et al., 2004), suggesting that ADAM8 plays a role in the pathogenesis of allergic asthma. The induction of experimental asthma in ADAM8 deficient mice almost suppresses the asthmatic phenotype, arguing for an essential role of ADAM8 in the pathogenesis of allergic asthma.

All these findings underline the importance of ADAM8 in inflammatory processes and the necessity to inhibit ADAM8 activity under those pathological conditions where ADAM8 activity has detrimental effects.

Recent attention has focussed on ADAM8 as a molecule upregulated in various tumours. ADAM8 is considered a prognostic marker for lung adenocarcinomas (Ishikawa et al., 2004) and renal cell carcinomas (Roemer et al., 2004). In addition, in brain tumours such as glioblastoma, oligoastrocytoma, and ependymoma, ADAM8 expression was increased compared to normal brain controls, and ADAM8 expression in glioblastoma correlates with malignancy and invasive activity (Wildeboer et al., 2006). In B-cells, ADAM8 cleaves the low-affinity IgE receptor (CD23, Fc'RII) suggesting a role in immune modulation (Fourie et al., 2003). Thus ADAM8 is implicated in allergy and inflammation by ectodomain shedding. A number of substrates of ADAM8 and their corresponding cleavage sites are known (Amour et al., 2000; Schlomann et al., 2002; Fourie et al., 2003; Naus et al., 2004, Naus et al., 2006).

Accordingly, inhibition of ADAM proteases is an attractive therapeutic target for many diseases. For example, WO 01/09189 discloses methods for diagnosing or treating neoplastic cell growth (e.g. certain cancers) involving agents which target ADAM8. WO 2005/090991 discloses methods for diagnosing or treating non-small cell lung cancer using agents such an ADAM8 siRNA that reduces expression of the ADAM8 gene. WO 2004/024089 discloses treating diseases associated with pathological neovascularisation (such as cancer, diabetic retinopathy and psoriasis) using agents which inhibit ADAMS or ADAM15. WO 01/94377 discloses that ADAM8 is also a therapeutic target for the treatment of allergy and asthma, whereas ADAM15 is a target for the treatment of osteoarthritis and atherosclerosis. The TNF-α-converting enzyme TACE (ADAM17) is a target for the treatment of inflammatory diseases including rheumatoid arthritis and ulcerative colitis (WO 97/35538 and Sekut et al. 1998, Expert Opin. Invest. Drugs. 7:1825-1839).

However, a number of the methods which have been identified to date for inhibiting metalloproteases such as ADAMs suffer from serious drawbacks. For instance, hydroxamate compounds such as marimastat and batimastat (BB-94) are typically broad-spectrum inhibitors and suffer from a lack of specificity for particular ADAMs. Consequently these compounds have shown deleterious side effects in clinical trials, which seriously restricts their usefulness as therapeutic agents. Therefore there is still a need for improved and more specific methods and reagents for inhibiting ADAM proteases, in particular for treating diseases such as cancer, inflammatory conditions and allergy.

SUMMARY OF THE INVENTION

Accordingly, in one aspect the present invention provides a method for inhibiting an ADAM protease, comprising inhibiting binding to an integrin-binding loop of a disintegrin domain in the ADAM protease.

In a further aspect, the invention provides a cyclic peptide of formula I:

(I)

wherein $X^0$, $X^1$, $X^2$ and $X^3$ each independently represents an amino acid residue, each amino acid residue in the ring being joined by a peptide bond;
the sequence $X^1$-$X^2$-$X^3$ is present in an integrin-binding loop of a disintegrin domain of an ADAM protease;
and n is 0 to 4;
or a pharmaceutically acceptable salt thereof.

In a further aspect, the invention provides a pharmaceutical composition comprising a cyclic peptide as defined above and a pharmaceutically acceptable excipient.

In a further aspect, the invention provides a cyclic peptide or pharmaceutical composition as defined above for use in medicine.

In a further aspect, the invention provides a cyclic peptide or pharmaceutical composition as defined above for use in treating a disease or condition associated with ADAM protease activity.

In a further aspect, the invention provides use of a cyclic peptide or pharmaceutical composition as defined above, for the preparation of a medicament for treating a disease or condition associated with ADAM protease activity.

In a further aspect, the invention provides a method for treating a subject suffering from a condition associated with ADAM protease activity, comprising administering to the subject a therapeutically effective amount of a cyclic peptide or pharmaceutical composition as defined above.

BRIEF DESCRIPTION OF THE FIGURES

FIG. 7A represents the "Swiss knife model". According to this model, the cyclic peptide interferes with the specific recognition of the substrate and thereby inhibits catalysis by the MP domain by binding to the disintegrin domain. FIG. 7B represents the "Aggregation model". According to this model the inhibitor (e.g. a cyclic peptide) blocks aggregation of the ADAM and its assembly into multimers (dimers or trimers), which is required for catalytic activity. Without being bound by theory, inhibitors according to the present invention which disrupt interactions involving the integrin-binding loop of ADAM proteases are believed to act according to the aggregation model shown in FIG. 7B, i.e. by inhibiting aggregation of monomer protease units and thereby preventing autocatalytic activation of the protease.

FIG. 9A and FIG. 9B shows alignments of the polypeptide sequences of human (FIG. 9A) and mouse (FIG. 9B) disintegrin domains (all gene bank accession numbers are given below). The integrin-binding loop flanked by two cysteine residues is boxed. The boxed sequences are preferred regions for targeting inhibitors according to the present invention. For instance, cyclic peptides comprising or based on these sequences may be used to inhibit specific ADAM proteases. Only ADAM15 contains an RGD sequence in its integrin-binding loop. The sequences of the ADAM proteases diverge considerably within the boxed region, allowing the design of inhibitors specific for each ADAM protease. Colons designated homologous amino acids, stars show perfect matches.

DETAILED DESCRIPTION OF THE INVENTION

Figure 1A:
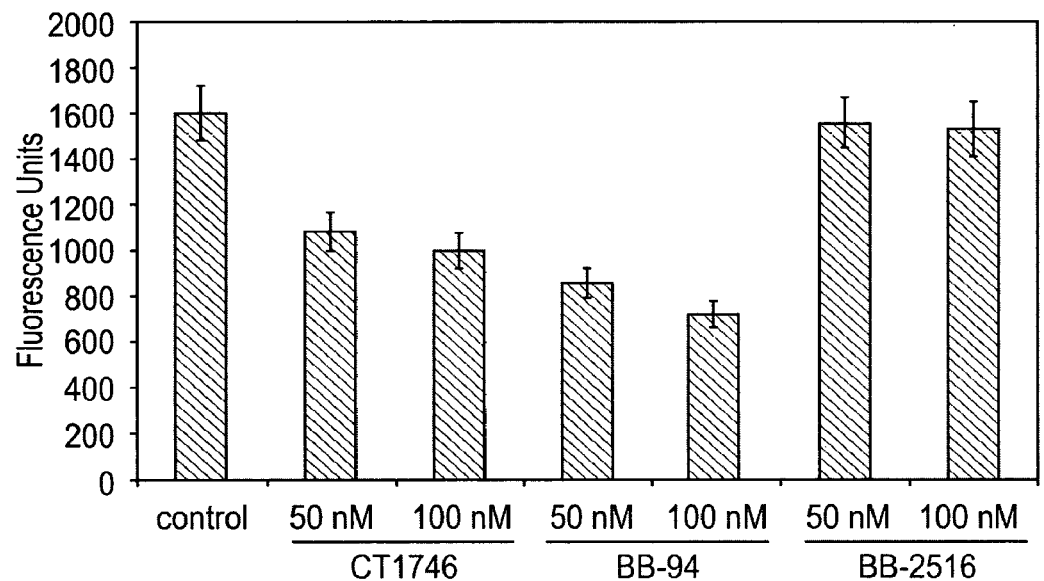
FIG. 1A shows the inhibition of ADAM8 proteolytic activity by the hydroxamates CT1746 (Celltech inhibitor), BB-94 ("Batimastate"), and BB-2516 ("Marimastate") which were used at concentrations indicated. BB-94 has an $IC_{50}$ of ~50 nM for the inhibition of ADAM8. Assays were performed as described below using CD23 as the substrate for ADAM8.

In one embodiment, the present invention relates to a method for inhibiting an ADAM protease. The method may be an in vitro method or an in vivo method. Typically the method involves inhibiting the proteolytic activity (i.e. the enzymatic activity) of the ADAM protease. Without being bound by theory, according to embodiments of the invention proteolytic activity may be inhibited by, for example, inhibiting aggregation (e.g. dimerisation or trimerisation) of the ADAM protease, and/or inhibiting autocatalytic activation of the ADAM protease. Disrupting binding to the integrin-binding loop of the disintegrin domain of the ADAM protease may inhibit aggregation (dimerisation/trimerisation) of protease monomers, thereby preventing autocatalytic activation of the ADAM protease and reducing its proteolytic activity.

Inhibition of ADAM protease activity may be measured by any suitable method. For example, a rate of proteolysis of a substrate of the ADAM protease may be measured in the presence and absence of the inhibitor. The substrate may, for example, be any peptide, polypeptide or protein sequence which is known to be cleaved by the ADAM protease. In one embodiment, inhibition of the ADAM protease may be measured using a substrate or method as described in WO 01/94377, the contents of which are incorporated herein by reference.

In some embodiments the activity of the ADAM protease in the presence of an inhibitor may be reduced by at least 10%, at least 30%, at least 50%, at least 70%, at least 90% or at least 95% compared to a control level of activity in the absence of the inhibitor.

By "ADAM protease" it is meant any member of the A Disintegrin and Metalloproteinase family of peptidases, including fragments and variants thereof having proteolytic activity. ADAM proteases may also be known as adamalysins or MDCs (metalloprotease disintegrin cysteine-rich proteins). The ADAM protease may be derived from any species, although human ADAM proteases are preferred. A characteristic feature of ADAM proteases is the presence of a metalloproteinase and a disintegrin domain. For example, the ADAM protease may be ADAM8, ADAM9, ADAM10, ADAM12, ADAM15, ADAM17, ADAM19, ADAM28 or ADAM33. In one embodiment, the ADAM protease is ADAM8 or ADAM10.

Inhibitors used in embodiments of the invention inhibit binding to an integrin-binding loop in a disintegrin domain of the ADAM protease. By this it is meant that the inhibitor blocks or disrupts an interaction between the integrin-binding loop and its cognate ligand. For instance, the inhibitor may reduce or prevent binding of the integrin-binding loop of an ADAM protease molecule to corresponding regions of a different ADAM protease molecule, thereby inhibiting aggregation (e.g. dimerisation/trimerisation).

By "integrin-binding loop" it is meant a region of the disintegrin domain which forms an exposed loop extending away from one surface of the folded ADAM polypeptide. This loop may also be known as a "disintegrin loop" and corresponds to a loop within which an RGD motif is found in snake venom disintegrins (see Bridges et al., 2003). The integrin-binding loop may mediate binding of ADAM proteases to integrins, as well as aggregation of ADAM monomers. Thus in some embodiments inhibitors according to the invention may also disrupt binding of ADAM proteases to integrins. However, according to embodiments of the present invention inhibition of proteolytic activity of the ADAM protease is of primary interest, rather than inhibition of ADAM/integrin interactions. Thus "integrin-binding loop" refers to a loop within a disintegrin domain having a structure homologous to that of e.g. an ADAM protease known to bind integrins (such as ADAM15 or ADAM28), or a snake venom disintegrin (such as echistatin, flavoridin or kistrin), regardless of whether known integrin ligands which bind to the loop exist.

Typically the integrin-binding loop of an ADAM protease comprises a 5 to 7 amino acid sequence (most commonly a 6 amino acid sequence) flanked by conserved cysteine residues. The first amino acid in this 5 to 7 amino acid sequence is commonly an R residue. The location of the integrin-binding loop in the disintegrin domain of a number of human and mouse ADAMs is shown in FIG. 9. The sequence of the integrin-binding loop of further ADAM proteases can be obtained by, for example, aligning their sequence with one or more of the sequences shown in FIG. 9, e.g. as described below. The presence of the conserved cysteine residues to either side of the 5 to 7 amino acid integrin-binding loop sequence is a characteristic feature which may assist in identification of the position of the loop within the disintegrin domain.

In preferred embodiments, the ADAM protease is one of those shown in FIG. 9. Thus in these embodiments, the integrin binding loop has one of the sequences as shown in the box in FIG. 9. Database accession numbers for the individual human and mouse ADAM proteases shown in FIG. 9 are listed below. The numbers in brackets below give the location of the disintegrin domain within the full-length polypeptide sequence in the database. Note that the numbering in FIG. 9 refers to the amino acid positions within the disintegrin domain.

Human ADAM8: NP001100 (417-492)
Human ADAM9: NP001005845 (423-498)
Human ADAM10: NP001101 (466-549)
Human ADAM12: NP067673 (448-508)
Human ADAM15: AAS73000 (430-504)
Human ADAM17: NP003174 (484-558)
Human ADAM19: NP150377 (439-500)
Human ADAM28: NP055080 (416-491)
Human ADAM33: NP079496 (426-501)
Mouse ADAM8: NP031429 (412-487)
Mouse ADAM9: NP031430 (423-498)
Mouse ADAM10: NP031425 (467-550)
Mouse ADAM12: NP031426 (446-506)
Mouse ADAM15: NP001032811 (431-505)
Mouse ADAM17: NP033745 (484-558)
Mouse ADAM19: NP033746 (440-500)
Mouse ADAM28: NP034212 (419-494)
Mouse ADAM33: NP291093 (427-502)

The polypeptide and nucleic acid sequences of many ADAM proteases are known and may be retrieved from publicly-accessible databases. Known polypeptide or polynucleotide sequences may be aligned with those of particular ADAM proteases and a degree of sequence identity or homology determined. Homology may be determined on the basis of percentage identity between two polypeptide (or DNA) sequences. In general the two sequences to be compared are aligned to give a maximum correlation between the sequences. The alignment of the two sequences is examined and the number of positions giving an exact nucleotide (or amino acid) correspondence between the two sequences determined, divided by the total length of the alignment multiplied by 100 to give a percentage identity figure. This percentage identity figure may be determined over the whole length of the sequences to be compared, which is particularly suitable for sequences of the same or very similar lengths and which are highly homologous, or over shorter defined lengths, which is more suitable for sequences of unequal length or which have a lower level of homology. For example, a degree of sequence identity to a nucleotide or amino acid sequence as defined herein may be determined over at least 15, at least 30, at least 50, or at least 100 residues.

Methods for aligning and comparing the identity of two or more sequences are well known in the art. Thus for instance, programs available in the Wisconsin Sequence Analysis Package, version 9.1 (Devereux J. et al, 1984) (available from Genetics Computer Group, Madison, Wis., USA), for example the programs BESTFIT and GAP, may be used to determine the percentage identity between two polypeptide (or polynucleotide) sequences. BESTFIT uses the "local homology" algorithm of Smith and Waterman (1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Needleman and Wunsch (1970). GAP is more suited to comparing sequences which are approximately the same length and an alignment is expected over the entire length. Preferably the parameters "Gap Weight" and "Length Weight" used in each program are 50 and 3 for polynucleotide sequences and 12 and 4 for polypeptide sequences, respectively. Preferably, percentage identities and similarities are determined when the two sequences being compared are optimally aligned.

Other programs for aligning or determining identity and/or similarity between sequences are also known in the art, for instance the BLAST family of programs (Karlin & Altschul, 1990, *Proc. Natl. Acad. Sci. USA* 87:2264-2268, modified as in Karlin & Altschul, 1993, *Proc. Natl. Acad. Sci. USA* 90:5873-5877, available from the National Center for Biotechnology Information (NCBI), Bethesda, Md., USA and accessible through the home page of the NCBI at http colon-slash-slash merops.sanger.ac.uk). These programs exemplify a preferred, non-limiting example of a mathematical algorithm utilized for the comparison of two sequences. Such an algorithm is incorporated into the NBLAST and XBLAST programs of Altschul, et al., 1997, *J. Mol. Biol.* 215:403-410. BLAST nucleotide searches can be performed with the NBLAST program to obtain nucleotide sequences homologous to a nucleic acid molecule of the invention. BLAST protein searches can be performed with the XBLAST program, to obtain amino acid sequences homologous to a protein molecule of the invention. To obtain gapped alignments for comparison purposes, Gapped BLAST can be utilized as described in Altschul et al., 1997, *Nucleic Acids Res*. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http colon-slash-slash merops.sanger.ac.uk. Another preferred non-limiting example of a mathematical algorithm utilized for the comparison of sequences is the algorithm of Myers and Miller, 1988, *CABIOS* 4:11-17. Such an algorithm is incorporated into the ALIGN program (version 2.0) which is part of the GCG sequence alignment software package.

Another non-limiting example of a program for determining identity and/or similarity between sequences known in the art is FASTA (Pearson W. R. and Lipman D. J., Proc. Nat. Acac. Sci., USA, 85:2444-2448, 1988, available as part of the Wisconsin Sequence Analysis Package). Preferably the BLOSUM62 amino acid substitution matrix (Henikoff S. and Henikoff J. G., Proc. Nat. Acad. Sci., USA, 89:10915-10919, 1992) is used in polypeptide sequence comparisons including where nucleotide sequences are first translated into amino acid sequences before comparison.

The percent identity between two sequences can be determined using techniques similar to those described above, with or without allowing gaps. In calculating percent identity, typically exact matches are counted.

Crystallographic structures of a number of proteases have been solved and are accessible through public databases, e.g. the Brookhaven protein database (Nucleic Acids Research, 28 pp. 235-242 (2000)). Such databases also include structural homologs in other enzyme classes and nonenzymatically active proteins of each class. Several tools are available to search public databases for structural homologues: SCOP—a structural classification of proteins database for the investigation of sequences and structures. (J. Mol. Biol. 247, 536-540, (1995)); CATH—Class, Architecture, Topology and Homologous superfamily: a hierarchical classification of protein domain structures (Orengo et al. (1997) Structure 5(8) 1093-1108); FSSP—Fold classification based on structure-structure alignment of proteins (Holm and Sander (1998) Nucl. Acids Res. 26 316-319); or VAST—Vector alignment search tool (Gibrat, Madej and Bryant (1996) Current Opinion in Structural Biology 6, 377-385). Two further databases which describe proteases are MEROPS (protease specific) at http colon-slash-slash merops.sanger.ac.uk (Rawlings, N. D., Morton, F. R. & Barrett, A. J. (2006) MEROPS: the peptidase database. Nucleic Acids Res 34, D270-D272) and BRENDA (enzymes) at http colon-slash-slash brenda.bc.uni-koeln.de (Nucleic Acids Res. 2004 Jan. 1; 32 Database issue:D431-3).

The above and other databases, alignment and comparison methods may be used to determine the location and sequence of the integrin-binding loop within the disintegrin domain of any particular ADAM protease, such that a selective or specific inhibitor (e.g. a cyclic peptide comprising a sequence within the integrin-binding loop or an antibody which specifically binds to the integrin-binding loop) for that ADAM protease may be identified.

Binding to the integrin-binding loop may be inhibited by various mechanisms. For example, in one embodiment an inhibitor is used which is capable of binding to the integrin-binding loop, thereby disrupting binding of the loop to its natural ligand (e.g. a disintegrin domain of a different molecule of the ADAM protease). For example, in one embodiment the inhibitor may be an antibody or a fragment thereof which specifically binds to the integrin-binding loop. In another embodiment the inhibitor may be based on an integrin to which the integrin-binding loop of the ADAM protease binds. Preferably the inhibitor is selective or specific for a particular ADAM protease, i.e. the inhibitor binds with higher affinity to the integrin-binding loop of one ADAM protease (or to a specific cognate binding site for the integrin-binding loop) compared to the integrin-binding loops of other ADAM proteases (or their ligands).

Thus in one embodiment the inhibitor may inhibit binding to the ADAM protease by competing with the integrin-binding loop for binding to its cognate ligand. For instance, the inhibitor may mimic the structure of the integrin-binding loop and bind to a natural ligand for the integrin-binding loop, thereby preventing the ADAM protease from associating with the ligand. In some embodiments, there may be a homophilic interaction between disintegrin domains or integrin-binding loops of individual ADAM polypeptide molecules. Thus where a ligand for the integrin-binding loop is an integrin-binding loop on another ADAM polypeptide molecule, a single inhibitor may both bind to the integrin-binding loop and mimic the structure of the integrin-binding loop (i.e. bind to a ligand of the integrin-binding loop). Typically the inhibitor disrupts interactions involving the integrin-binding loop which are involved in association and/or aggregation of ADAM monomers.

In one embodiment, the inhibitor is a peptide. The peptide may mimic the structure of the integrin-binding loop. For example, the peptide may comprise an amino acid sequence present in the integrin-binding loop. In particular embodiments, the peptide comprises a sequence of 2 to 15, 2 to 10, 3 to 10, 3 to 7, 5 to 7 or 3 to 5 amino acid residues present in the integrin-binding loop of the ADAM protease. For example, in specific embodiments the peptide may comprise a sequence of 2, 3, 4, 5, 6, 7 or more amino acid residues which is present in the integrin-binding loop.

Typically the entire sequence of the peptide is present in the integrin-binding loop, and so the length of the peptide is the same as the length of the sequence present in the integrin-binding loop. However, in some embodiments additional amino acid residues may be present in the peptide which are not present in the integrin-binding loop, e.g. at one or both ends of the peptide. For example, the peptide may be 5 amino acids in length and comprise a sequence of 3 amino acid residues present in the integrin-binding loop, plus 2 further amino acids which are not present in the integrin-binding loop of the ADAM protease. Preferably the peptide comprises at least the 3 amino acid residues within the integrin-binding loop of an ADAM protease which correspond to the position of the RGD sequence of snake venom disintegrins. This RGD sequence is also present in ADAM15. The location of this 3 amino acid motif may be determined, for example, by aligning a particular ADAM protease disintegrin domain sequence to that of snake venom disintegrins and/or ADAM15, for instance as described in Bridges et al. (2003). In a number of ADAM proteases, this 3 amino acid motif which is involved in integrin binding is at the C-terminal end of the integrin-binding loop, i.e. the 3 amino acid residues which are immediately upstream of the cysteine residue which flanks the integrin-binding loop on the C terminal side.

In some embodiments the peptide is a cyclic peptide. The cyclic peptide may comprise a sequence of amino acid residues present in the integrin-binding loop and have a length as defined above in relation to peptides in general. Particularly preferred lengths for the cyclic peptide are 3 to 7 (e.g. 5 to 7) amino acid residues, e.g. 6 amino acid residues. The residues at each end of the linear peptide sequence found in the integrin-binding loop may be joined to form the cyclic peptide. For example, the cyclic peptide may comprise a linear sequence of 3 to 7 amino acid residues (e.g. 6 amino acid residues) present in the integrin-binding loop, wherein the N and C terminal residues of the linear sequence are joined by a peptide bond. Short cyclic peptides may be most effective in mimicking the structure of the integrin-binding loop and thereby competing for ligand binding.

The peptide, e.g. cyclic peptide, may comprise one or more β-amino acid residues. In the 20 standard a amino acids both the carboxylic acid group and the amino group are bonded to the same (a) carbon, whereas in β amino acids, the amino group is bonded to the β carbon (which is found in each of the 20 standard amino acids except glycine). Most β amino acids have a chiral β carbon atom, whereas in a amino acids the α carbon is typically chiral. The inclusion of one or more β-amino acid residues in the peptide favours the formation of a turn which may present the peptide sequence in a secondary structure more closely resembling that of the integrin-binding loop in ADAM proteases. Peptides comprising β-amino acid residues may also be more stable against proteolytic degradation in vitro and in vivo than purely a amino acid-containing peptides, which may enhance their pharmacokinetic properties and therapeutic efficacy when administered to a patient.

Preferably the peptide comprises 6 amino acid residues and a β-amino acid is present as the $3^{rd}$ amino acid residue from the N-terminal. In the case of a cyclic peptide comprising 6 amino acid residues which correspond to the sequence of an integrin-binding loop of a particular ADAM protease, the β-amino acid may be present as the $3^{rd}$ amino acid residue counting in a sequence starting from the residue which is at the N-terminal end of the integrin-binding loop in the ADAM protease.

In specific embodiments, the ADAM protease is one of those whose disintegrin domain sequence is given in FIG. 9 and the peptide comprises a subsequence from the disintegrin domain of that particular ADAM protease, the subsequence being shown within the box in FIG. 9. For instance where inhibition of ADAM8 is desired, the peptide may comprise the sequence RPKKDM (SEQ ID NO:2), RLSKDK (SEQ ID NO:3), KDK or KDM. The variation in sequence within the integrin-binding loop of ADAM proteases allows specific inhibitors (i.e. inhibitors which discriminate between ADAM proteases by selectively binding to particular ADAMs but not to others) to be designed.

Thus in one aspect, the present invention provides a cyclic peptide having the following general formula (I):

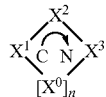
(I)

wherein $X^0$, $X^1$, $X^2$ and $X^3$ each independently represents an amino acid residue, each amino acid residue in the ring being joined by a peptide bond;
the sequence $X^1$-$X^2$-$X^3$ is present in an integrin-binding loop of an ADAM protease;
and n is 0 to 4.

Preferably n is 2 to 4, more preferably n is 3, i.e. formula (I) represents a cyclic peptide comprising 5 to 7, more preferably 6 amino acid residues. Where n is greater than 1, each $X^0$ may be the same or different. When n is 0, there is a direct peptide bond between $X^1$ and $X^3$.

Each $X^0$ may be an alpha or a beta amino acid residue. The term "amino acid residue" as used herein includes modified amino acid residues, e.g. an N-methylated amino acid residue or an acetylated amino acid residue. Each amino acid may be a D-amino acid or an L-amino acid residue, although L-amino acids are preferred. Preferably $[X^0]_n$ represents a sequence of 2 to 4, more preferably 3 amino acid residues which is present in the integrin-binding loop of the ADAM protease which comprises the sequence $X^1$-$X^2$-$X^3$, e.g. the sequence $[X^0]_n$-$X^1$-$X^2$-$X^3$ is a 6 amino acid sequence present in the integrin-binding loop of the ADAM protease.

Preferably the sequence $X^1$-$X^2$-$X^3$ in formula (I) is present in an integrin-binding loop of an ADAM protease at a position corresponding to the location of the RGD sequence in snake venom disintegrins and human ADAM15. Preferred $X^1$-$X^2$-$X^3$ sequences are: TSE, KDE, KDM, RGD, SNS, ARQ, MGD, DSD, NAT, KDK, VRQ, ATD & TDD, more preferably TSE, KDE, KDM, SNS, ARQ, MGD, DSD, NAT, KDK, VRQ, ATD & TDD, more preferably TSE, KDE, KDM, KDK or DSD, most preferably KDM or KDK.

Preferably $X^1$ is an arginine (R) residue. In certain embodiments, the cyclic peptide of formula (I) comprises one of the following amino acid sequences: RGKTSE (SEQ ID NO:4), RPAKDE (SEQ ID NO:5), RPKKDM (SEQ ID NO:2), RPTRGD (SEQ ID NO:6), RDSSNS (SEQ ID NO:7), REQARQ (SEQ ID NO:8), RQAMGD (SEQ ID NO:9), RDDSD (SEQ ID NO:10), QEAINAT (SEQ ID NO:11), RLSKDK (SEQ ID NO:3), RAAKDE (SEQ ID NO:12), RGSSNS (SEQ ID NO:13), REQVRQ (SEQ ID NO:14), RPAATD (SEQ ID NO:15), & RPPTDD (SEQ ID NO:16), more preferably RPKKDM (SEQ ID NO: 2) or RLSKDK (SEQ ID NO: 3).

The arrow in formula (I) represents the C→N peptide bond direction, i.e. a carbonyl group of $X^1$ is bound to a N atom of $X^2$, and a carbonyl group of $X^2$ is bound to a N atom of $X^3$.

Preferably one or more β-amino acids are present in the cyclic peptide of formula (I), for instance one of the $X^0$ residues may be a β-amino acid. Thus in one embodiment the cyclic peptide has a formula (II):

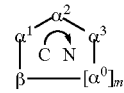
(II)

wherein $\alpha^0$, $\alpha^1$, $\alpha^2$ and $\alpha^3$ each independently represents an alpha-amino acid residue;
β represents a beta-amino acid residue;
each amino acid residue in the ring being joined by a peptide bond;
m is 1 to 3, preferably 2;
at least the amino acid sequence $\alpha^1$-$\alpha^2$-$\alpha^3$, more preferably a sequence equivalent to the sequence $[\alpha^0]_m$-β-$\alpha^1$-$\alpha^2$-$\alpha^3$, is present in an integrin-binding loop of an ADAM protease.

By "a sequence equivalent to the sequence $[\alpha^0]_m$-β-$\alpha^1$-$\alpha^2$-$\alpha^3$", it is meant that the integrin-binding loop of the ADAM protease contains an α-amino acid residue corresponding to the β-amino acid residue present in cyclic peptide, i.e. the same amino acid residue is present at this position in both the ADAM protease and the cyclic peptide, the alpha form being present in the ADAM protease and the beta form of that amino acid being present in cyclic peptide.

In particular embodiments, the sequences $\alpha^1$-$\alpha^2$-$\alpha^3$ and $[\alpha^0]_m$-β-$\alpha^1$-$\alpha^2$-$\alpha^3$ may be the specific sequences defined above for $X^1$-$X^2$-$X^3$ and $[X^0]_n$-$X^1$-$X^2$-$X^3$ respectively, for instance comprising a single β-amino acid residue in place of a corresponding α-amino acid residue. In particular, the cyclic peptide may be cyclo(RGkTSE) (SEQ ID NO: 40), cyclo(RPaKDE) (SEQ ID NO: 41), cyclo(RPkKDM) (SEQ ID NO: 42), cyclo(RPtRGD) (SEQ ID NO: 43), cyclo(RDsSNS) (SEQ ID NO: 44), cyclo(REqARQ) (SEQ ID NO: 45), cyclo(RQaMGD) (SEQ ID NO: 46), cyclo(RdDSD) (SEQ ID NO: 47), cyclo(QEAiNAT) (SEQ ID NO: 48), cyclo(RLsKDK) (SEQ ID NO: 49), cyclo(RAaKDE) (SEQ ID NO: 50), cyclo(RGsSNS) (SEQ ID NO: 51), cyclo(REqVRQ) (SEQ ID NO: 52), cyclo(RPaATD) (SEQ ID NO: 53) or cyclo(RPpTDD) (SEQ ID NO: 54), wherein a lower case letter represents a beta amino acid (upper case letters representing alpha amino acids). More preferably the cyclic peptide is cyclo(RPkKDM) (SEQ ID NO: 42) or cyclo(RLsKDK) (SEQ ID NO: 49), i.e. cyclo(Arg-Pro-{β-Lys}-Lys-Asp-Met) (SEQ ID NO: 42) or cyclo(Arg-Leu-{β-Ser}-Lys-Asp-Lys) (SEQ ID NO: 49).

Thus in one embodiment, the cyclic peptide comprises a compound of formula (III):

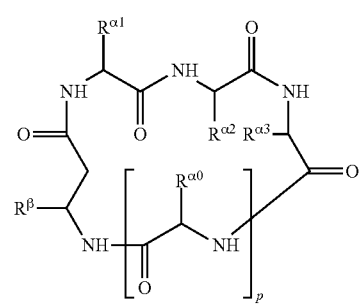
(III)

wherein $R^{\alpha 0}$, $R^{\alpha 1}$, $R^{\alpha 2}$ and $R^{\alpha 3}$ each independently represents an alpha-amino acid side-chain;
$R^\beta$ represents a beta-amino acid side-chain;
p is 1 to 3, preferably 2;
$R^{\alpha 1}$, $R^{\alpha 2}$ and $R^{\alpha 3}$ are selected such that the cyclic peptide comprises a 3 amino acid sequence present in an integrin-binding loop of an ADAM protease;
or a pharmaceutically acceptable salt thereof.

Preferably p, $R^{\alpha 0}$ and $R^\beta$ are also selected such that the cyclic peptide comprises a sequence equivalent to a 5 to 7 amino acid residue sequence present in an integrin-binding loop of an ADAM protease, most preferably one of the specific 5 to 7 amino acid sequences referred to above and shown boxed in FIG. 9. Where p is greater than 1, each $R^{\alpha 0}$ may be the same or different. $R^{\alpha 1}$, $R^{\alpha 2}$ and $R^{\alpha 3}$ may be selected such that they comprise the side-chains of amino acid residues present in an integrin-binding loop of an ADAM protease at a location equivalent to the RGD sequence in the integrin-binding loop of snake venom disintegrins and human ADAM15.

The amino acid sidechains $R^{\alpha 0}$, $R^{\alpha 1}$, $R^{\alpha 2}$ and $R^{\alpha 3}$ may be any of those of e.g. the 20 naturally occurring amino acids. The amino acid sidechain $R^{\beta}$ may be, for example, a sidechain of a beta-amino acid corresponding to one of the 20 standard (alpha) amino acids, i.e. wherein the beta-amino acid sidechain corresponds to the alpha amino acid sidechain minus a $CH_2$ group.

Preferably each of the amino acid residues in the peptide is derived from an L-amino acid. In some embodiments, one or more D-amino acid residues may be present.

The peptide inhibitors of the present invention, e.g. the compounds of formulae I to III, may exist in free or salt form. Examples of pharmaceutically acceptable salts of the peptides, e.g. the compounds of the formula I to III, include salts with inorganic acids, such as hydrochloride, hydrobromide and sulfate, salts with organic acids, such as acetate, fumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the above peptides of the present invention encompass hydrate and solvate forms.

Peptides such as cyclic peptides according to the invention may be synthesised according to standard techniques such as the solid phase method with Fmoc protected amino acids. Cyclic peptides may in general be synthesised according to the method described in Malesevic et al. (2004), Journal of Biotechnology 112, 73-77. β-amino acids may be synthesised and incorporated into the peptide by, for example, solid phase Arndt-Eistert homologation (Marti et al., 1997). Alternative methods for the synthesis of peptides containing beta-amino acids are described or referred to in Curr Med Chem 6(10):905-25 (1999); J Org Chem 70(24): 9798-808 (2005); J Am Chem Soc 127(38):13271-80 (2005); and J Comp Chem 15; 27(1):20-38 (2006).

In further embodiments, the inhibitor may be an alternative agent which mimics the structure of the integrin-binding loop of an ADAM protease, including any known peptidomimetics. In general, when referring to "peptide" or "cyclic peptide" herein it is intended to cover modified peptides, including those having appropriate modifications which may be made in order to ensure, for example, better solubility, uptake or bioavailability. The peptides may also be modified, for example, by the addition of one or more groups which are used to label the peptide (e.g. a fluorescent label) or conjugate the peptide to a further molecule, or by the inclusion of non-naturally occurring amino acid residues.

In certain embodiments, the inhibitor may be an agent which binds selectively or specifically to a peptide sequence within the integrin-binding loop of an ADAM protease. For instance, in one embodiment, the inhibitor is an antibody or an antibody fragment. Suitable inhibitors thus comprise an antibody, including, but not limited to, a monoclonal antibody, a polyclonal antibody, an antibody fragment (e.g., Fab, Fab', F(ab')2, Fv), a single chain antibody (e.g. scFv), a nanobody (e.g. as disclosed in WO2004/041862), a camelid antibody (e.g. as disclosed in EP0584421), a domain antibody (e.g. as disclosed in WO91/002078), a humanized antibody, a chimeric antibody, or a mutant thereof, a fusion protein comprising an antibody portion, or any other polypeptide that comprises an antigen recognition site of the required specificity. The antibody may be murine, rat, rabbit, chicken, human, or of any other origin (including humanized antibodies).

Other suitable inhibitors include or may be based on diabodies (PNAS 90, 6444-6448, 1993), affibodies (WO95/19374), foldamers (U.S. Pat. No. 6,060,585), major histocompatability class I and class II molecules (U.S. Pat. No. 5,976,551, WO00/15665), T-cell receptors (Cell Immunol., 192 (2), 175-84, 1999), fibronectins e.g. trinectins (U.S. Pat. No. 6,818,418, WO98/56915), lipocalins e.g. anticalins (WO99/16873), bacterial receptors (WO95/19374, WO0063243), chaperons and chaperonins (Biochem. J., 15 (333) 233-42, 1998), RNA, DNA and peptide aptamers (Nature 346 (6287), 818-22, 1990), molecular imprinted polymers (MIPs) (Nature 361, 645-647, 1993), diketopiperazine receptors (Chem. Eur. J., 7, 3342-3347, 2001), and mimetic ligands (WO2006/131768).

In general, antibodies and other biological agents may be cloned, expressed as heterologous proteins and selected by methods such as phage display and panning, ribosome display and screening, periplasmic expression with cytometric screening (PECS) and conventional expression, purification and affinity testing procedures. Selection procedures for DNA, RNA or peptide aptamers may for example involve a number of rounds of selection, PCR based amplification of selected sequences and re-selection. Inhibitors such as MIPs and mimetic ligands may be made as combinatorial libraries and then screened for affinity a specific polypeptide sequence present in the integrin-binding loop of an ADAM protease.

Antibodies against the integrin-binding loop of specific ADAM proteases may be generated by well-established methods. Methods for synthesizing polypeptides and immunizing a host animal are well known in the art. Typically, the host animal is inoculated intraperitoneally with an amount of immunogen (i.e. a peptide comprising a sequence within the integrin-binding loop of an ADAM protease), and (in the case of monoclonal antibody production) hybridomas prepared from its lymphocytes and immortalized myeloma cells using the general somatic cell hybridization technique of Kohler, B. and Milstein, C. (1975) Nature 25 6:495-497.

Hybridomas that produce suitable antibodies may be grown in vitro or in vivo using known procedures. Monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen.

If desired, the antibody (monoclonal or polyclonal) of interest may be sequenced and the polynucleotide sequence may then be cloned into a vector for expression or propagation. The sequence encoding the antibody may be maintained in a vector in a host cell and the host cell can then be expanded and frozen for future use. In one embodiment, the polynucleotide sequence may be used for genetic manipulation to "humanize" the antibody or to improve the affinity, or other characteristics of the antibody.

Phage display technology, for instance as described in U.S. Pat. No. 5,565,332 and other published documents, may be used to select and produce human antibodies and antibody fragments in vitro, from immunoglobulin variable (V) domain gene repertoires from unimmunized donors. For example, existing antibody phage display libraries may be panned in parallel against a large collection of synthetic polypeptides. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties.

Antibodies may be made recombinantly and expressed using any method known in the art. For instance, antibodies may be isolated from host animals, the gene sequence obtained, and the gene sequence used to express the antibody recombinantly in transfected host cells (such as E. coli cells, simian COS cells, Chinese hamster ovary (CHO) cells, or myeloma cells that do not otherwise produce immunoglobulin protein). Another method that may be employed is to express the antibody sequence in plants (e.g., tobacco), transgenic milk, or in other organisms.

The binding specificity of antibodies and other inhibitors of the invention may be characterized using methods well-known in the art. For example, suitable methods include phage display (as discussed above), epitope mapping, solving the crystal structure of an antibody-antigen complex, competition assays, gene fragment expression assays, and synthetic polypeptide-based assays.

The ADAM protease inhibitors of the present invention may be combined with any pharmaceutically acceptable excipients in pharmaceutical compositions for medical or veterinary use. The methods and ADAM protease inhibitors of the present invention may be used to prevent and/or treat conditions and diseases associated with ADAM protease activity. These conditions include those where ADAM protease activity is implicated in the pathological process, for instance in the initiation, maintenance or progress of the disease, as well as those where ADAM protease activity may not be directly responsible for the pathology but inhibition of an ADAM protease has a beneficial or ameliorative effect. In one embodiment the disease is associated with elevated ADAM protease activity, for instance increased expression of an ADAM protease in a subject suffering from the disease (e.g. increased ADAM expression in a diseased tissue). In particular embodiments the disease may be cancer, an inflammatory condition or allergy. Increased ADAM expression in diseased tissues, e.g. a tumor or inflamed joint, has been observed in previous studies and a skilled person can easily perform similar tests to determine whether a particular condition is associated with elevated ADAM protease activity.

Therapeutic formulations comprising an inhibitor according to the present invention may be prepared, for example, by mixing the inhibitor having a desired degree of purity with optional pharmaceutically acceptable carriers, excipients or stabilizers (Remington's Pharmaceutical Sciences, 16th edition, Osol, A. Ed. [1980]), e.g. in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such asoctadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatinmicrocapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

The formulations to be used for in vivo administration should be sterile. This is readily accomplished by filtration through sterile filtration membranes.

Sustained-release preparations may be prepared. Suitable examples of sustained-release preparations include semipermeable matrices of solid hydrophobic polymers containing the inhibitor, which matrices are in the form of shaped articles, e.g., films or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L glutamate, non-degradable ethylene-vinyl acetate, degradable lactic acid-glycolic acid copolymers (e.g. injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. In order to prevent or reduce denaturation or aggregation of inhibitors in the body, a stabilization method may be used. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The inhibitors of the present invention may be used to treat various conditions in which ADAM proteases are implicated, including those characterized by overexpression and/or activation of ADAM proteases. In particular, the inhibitors may be used to prevent or treat a disease associated with cell migration or cell invasiveness, for instance a cancer (particularly metastatic cancer) or an inflammatory condition (e.g. a condition associated with migration of immune cells such as leukocytes). Exemplary conditions or disorders to be treated with such inhibitors include, but are not limited to, benign or malignant tumors (e.g., renal, liver, kidney, bladder, brain, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The inhibitors of the present invention, e.g., antibodies, may be administered to a mammal, preferably a human, in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Where the inhibitor is a polypeptide (e.g. an antibody), intravenous administration is preferred.

Other therapeutic regimens may be combined with the administration of the inhibitory agents. For example, a cancer patient to be treated with an inhibitor of the present invention may also receive radiation therapy. Alternatively, or in addition, a chemotherapeutic agent may be administered to the patient. Preparation and dosing schedules for such chemotherapeutic agents may be used according to manufacturer's instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the inhibitor, e.g., cyclic peptide or antibody, or may be given simultaneously therewith. The antibody may be combined with an anti-oestrogen compound such as tamoxifen or an anti-progesterone such as onapristone (see, EP 616812) in dosages known for such molecules. It may be desirable to also administer antibodies against other tumor associated antigens, such as antibodies which bind to the ErbB2, EGFR, ErbB3, ErbB4, or vascular endothelial factor (VEGF).

In particular embodiments, it may be beneficial to also administer one or more further therapeutic agents, e.g. one or more cytokines or a growth inhibitory agent, together with an inhibitor of the present invention. The ADAM protease inhibitor of the present invention may be administered simultaneously, separately or subsequently to the administration of a further therapeutic agent. Suitable dosages for the further therapeutic agent are those presently used and may be lowered due to the combined action (synergy) of the further therapeutic agent and the ADAM protease inhibitor.

For the prevention or treatment of disease, the appropriate dosage of the ADAM protease inhibitor of the present invention, e.g., a cyclic peptide or an antibody as described herein will depend on the type of disease to be treated, as defined above, the severity and course of the disease, whether the inhibitor is administered for preventive or therapeutic purposes, previous therapy, the patient's clinical history and response to the inhibitor, and the discretion of the attending physician. The agent is suitably administered to the patient at one time or over a series of treatments.

For example, depending on the type and severity of the disease, about 1 µg/kg to 10 mg/kg (e.g. 0.1-10 mg/kg) of the ADAM protease inhibitor may be administered to the patient, whether, for example, by one or more separate administrations, or by continuous infusion. A typical daily dosage might range from about 1 µg/kg to 10 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

In addition, an agent that inhibits the activity of an ADAM protease (e.g. ADAM8) can be used to treat various diseases of inflammation. Initiating, exacerbating, or ongoing events in diseases of both acute and chronic inflammation involve the trafficking and migration of various populations of leukocytes, for example monocytes, into and out of tissue resulting in tissue damage. Inhibiting the migration, trafficking, and tissue destruction by leukocytes by inhibiting the ADAM protease (e.g. ADAM8) mitigates the inflammatory process. Diseases such as psoriasis, dermatitis, inflammatory bowel disease, arthritis, multiple sclerosis and chronic obstructive pulmonary diseases are examples of diseases, which can be treated, with an inhibitor of an ADAM protease (e.g. ADAM8). In one embodiment the disease to be treated is a (e.g. inflammatory or allergic) condition associated with CD23 release. In this embodiment, the inhibitor may be, for example, an ADAM8 inhibitor, where ADAM8 activity promotes disease symptoms and/or progression by cleaving CD23.

Additional examples of such diseases include T cell inflammatory responses such as inflammatory skin diseases including responses associated with inflammatory bowel disease (such as Crohn's disease and ulcerative colitis); adult respiratory distress syndrome; meningitis; encephalitis; uveitis; allergic conditions such as eczema and asthma; conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; chronic obstructive pulmonary disease (COPD); bronchitis; insulinitis; rhinitis; urticaria; glomerulonephritis; diseases involving leukocyte diapedesis; CNS inflammatory disorder; multiple organ injury syndrome secondary to septicaemia or trauma; autoimmune hemolytic anemia; myethemia gravis; antigen-antibody complex mediated diseases; nephrotic syndrome; malignancies (e.g. B-cell malignancies such as chronic lymphocytic leukemia or hairy cell leukemia); all types of transplantations, including graft vs. host or host vs. graft disease; HIV and rhinovirus infection; pulmonary fibrosis; invasion of tumor cells into secondary organs.

These diseases can be treated using the formulations, routes of administration, doses and dosing formats as discussed above.

Preferred diseases to be treated (e.g. with an inhibitor of ADAMS) are neoplastic conditions such as cancer, especially brain (e.g. glioblastoma, oligoastrocytoma and ependymoma), prostate, lung (e.g. lung adenocarcinomas), kidney (e.g. renal cell carcinomas) and pancreatic tumours. Other preferred conditions to be treated include asthma and allergic reactions. Most preferably the condition to be treated is a brain tumour e.g. glioma.

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually an anti-tumor agent that is capable of interfering with the activity of a gene product identified herein, e.g., an antibody. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Embodiments of the invention will now be further described with reference to the following specific examples, which are provided for illustrative purposes only and do not limit the scope of the invention.

EXAMPLES

Due to the impact of ADAM proteases, in particular ADAM8, in conditions such as cancer cell migration, asthma and allergic responses, it is highly desirable to obtain specific inhibition of a particular ADAM (e.g. ADAM8) protease activity. Under physiological conditions, inhibition of ADAM8 in vivo is not expected to have any severe side effects, as mice deficient in the Adam8 gene show no abnormalities during development or homeostasis (Kelly et al., 2005). The expression of ADAM8 in the diseased organism is induced by inflammatory stimuli (e.g. Tumour Necrosis Factor alpha, Schlomann et al., 2000). The DC domain has a significant effect on the catalytic activity of ADAM8, as reflected by prodomain removal: ADAM8 produced in transfected cells with the DC domain appears to be completely processed by prodomain removal, whereas the ADAM8 MP domain on its own shows a low degree of autocatalysis (Schlomann et al., 2002). Therefore the Disintegrin-cysteine-rich (DC) domain could be a potential target for inhibition of ADAM8 activity, in addition to the Metalloprotease (MP) domain. However, no method for inhibiting ADAM8 activity via the DC domain has described, due to a lack of target sites within the domain and inhibitors which specifically target such sites.

The present inventor identified that the disintegrin domain of human ADAM15 contains an RGD sequence in one of the loop structures, called the integrin binding loop, a 6 amino acid stretch flanked by conserved cysteine residues. RGD peptides are known to be involved in binding to integrins and the crystal structure of an RGD peptide binding to the integrin αVβ3 has been disclosed (Xiong et al., 2002). The present inventors aimed in one embodiment to target the ADAM8 DC domain (and thereby inhibit ADAM8 protease activity) with small cyclic peptides which mimic the structure of ADAM8 at a location in its integrin-binding loop which corresponds to the RGD sequence in ADAM15. The 3 amino acid motif KDK in the integrin binding loop of ADAM8 is expected to be exposed to the outside of a loop, by comparison to the highly homologous sequence of ADAM28 (see Bridges et al., 2003).

In one embodiment, the present inventor tested peptides which present this 3 amino acid motif by means of a cyclic confirmation. In addition, the incorporation of beta-amino acids improved the ability of the cyclic peptides to inhibit ADAM8. Several conformational variants were used to test the effect of cyclic peptides in in vivo assays, initially targeting the effect of cell adhesion mediated by the ADAM8 DC domain.

The following examples demonstrate that the protease activity of ADAM proteases, resulting in ectodomain shedding of various membrane proteins with function in inflammation, allergy, and tumour cell migration, can be targeted directly by compounds directed at the DC domain.

Example 1A

Synthesis of Cyclic Peptides

Figure 5:
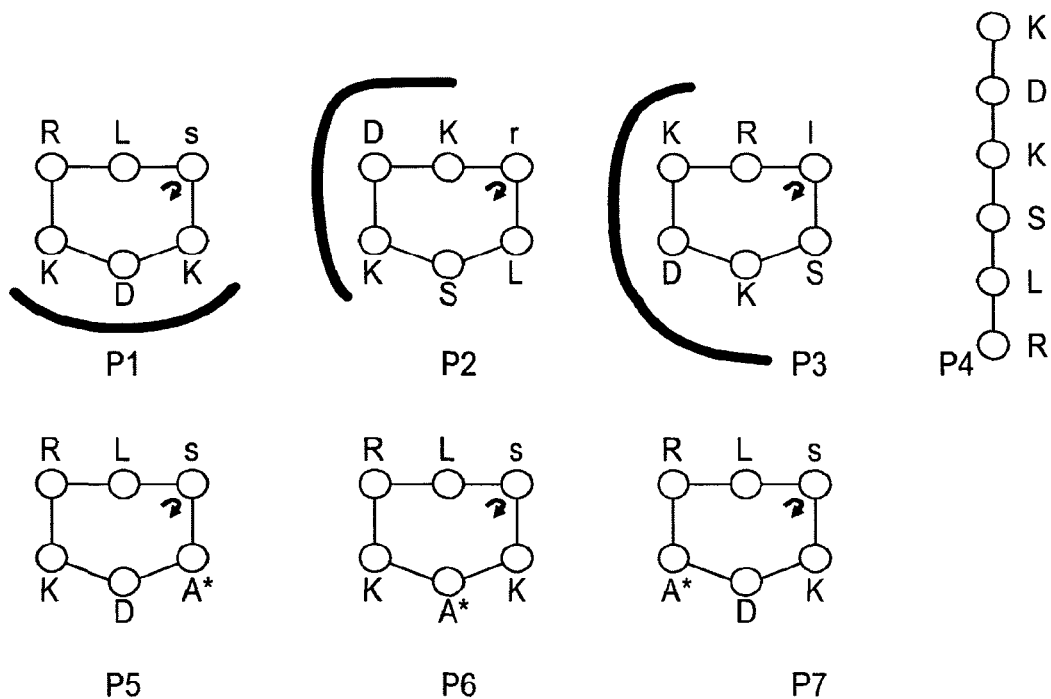
FIG. 5 is a schematic diagram representing the structures of peptides P1 to P7. P1, 2, 3, and 4 are conformational variants each comprising the 3 amino acid motif KDK. The potential contact sphere between the integrin binding loop of the ADAM protease and each of the cyclic peptides P1 to P3 is shown as a bold line. The difference in the conformation of the cyclic peptides is indicated by the position of the β-amino acid which is able to mimic a turn (represented by the arrow in the Figure). The β-amino acids are represented by lower case letters (s=β-serine; 1=β-Leucine; r=β-arginine). A clockwise rotation around P1-P3 and P5-P7 represents the direction of C→N peptide bonds, i.e. the direction which corresponds to a transition from the N-terminal to the C-terminal of the corresponding linear peptide.
Figure 6:
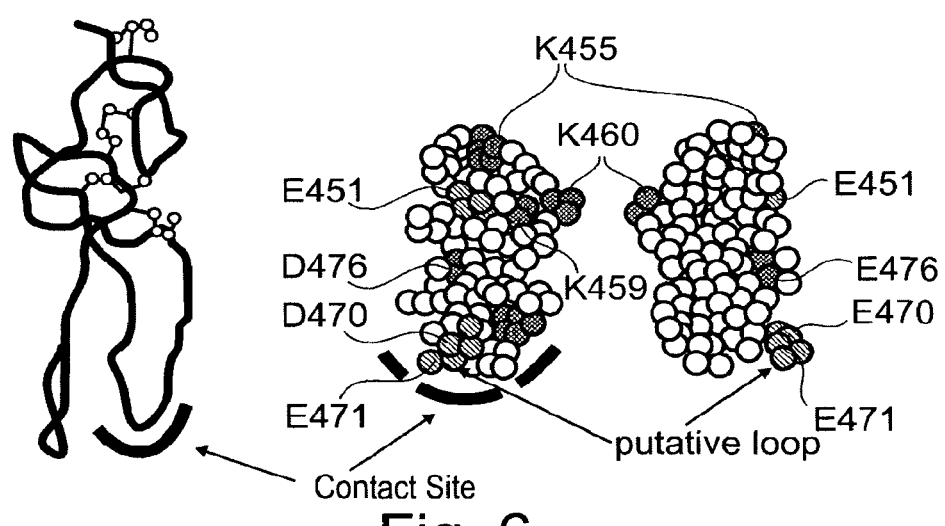
FIG. 6 shows a molecular model of the integrin binding loop of ADAM28 based on similar structures in snake venom metalloproteases. ADAM28 comprises a KDE motif in its integrin-binding loop. The loop with this 3 amino acid motif is exposed to the outside and is similar to the arrangement of the KDK motif in ADAM8.
Figure 7:
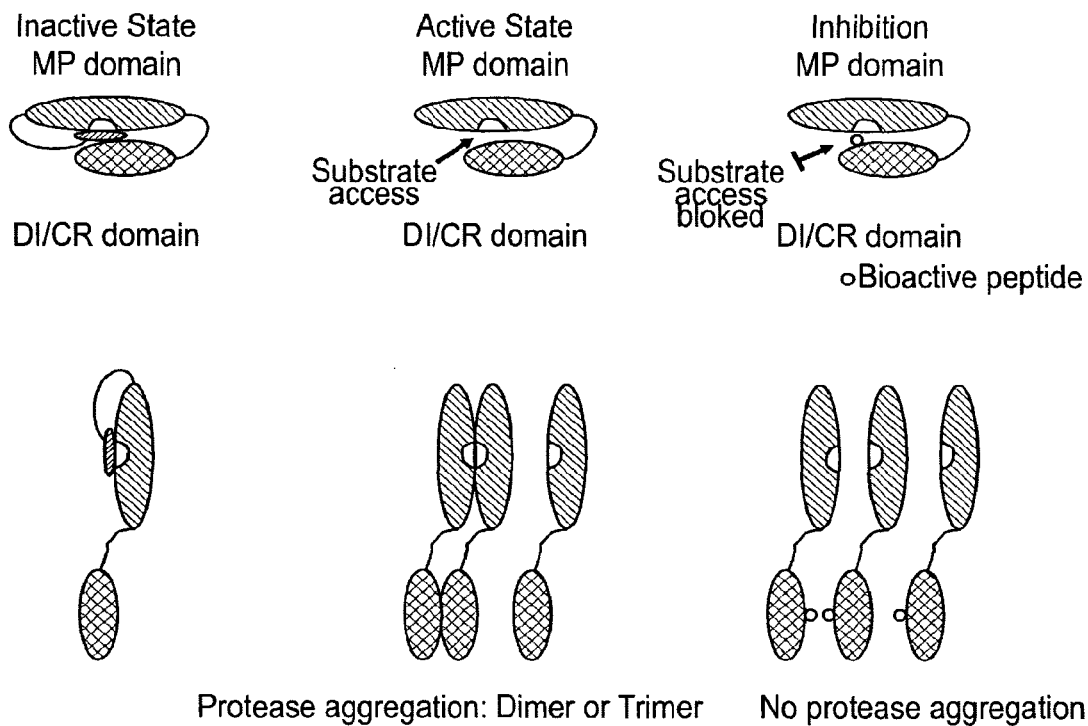
FIG. 7 shows two theoretical mechanisms for the inhibition of ADAM8 by an inhibitor.

In the following example, a series of peptides were synthesised in order to test their activity as inhibitors of ADAM proteases. The structures of the peptides are shown in Table 1 and FIG. 5.

Each peptide comprises 6 amino acid residues. Peptides P1 to P4 have the sequence RLSKDK (SEQ ID NO: 3), which is found in the integrin binding loop of the disintegrin domain of murine ADAM8. The KDK sequence of ADAM8 is at an equivalent position to the RGD sequence found in the integrin-binding loop of ADAM15. Peptides P1 to P3 are cyclic peptides comprising this motif, whereas P4 is a linear peptide with the KDK sequence at the C terminal. Each of P1 to P3 comprises a single β-amino acid, the position of which differs between the three peptides.

Each of peptides P5, P6 and P7 is a cyclic peptide which differs in sequence from peptide P1 at one amino acid position within the KDK motif found in P1. Each of P5 to P7 comprises a single β-amino acid residue at the same position as in P1.

Cyclic peptides were synthesised by the solid phase method with Fmoc protected amino acids using dicyclohexylcarbodiimide/1-hydroxybenzotriazole as coupling reagents. After release from the resin by mild acid treatment, cyclisation was achieved in high dilution with diphenylphosphoryl azide pH8.5, followed by removal of side chain protecting groups under strong acidic conditions. The peptides were then purified by high performance liquid chromatography and characterised by mass spectrometry. Incorporation of β-amino acids was achieved by solid phase Arndt-Eistert homologation, as described by Marti et al., 1997 using Wang resin as linker.

The usage of β-amino acids limits the conformational freedom of the three amino acid target motif in the peptide. In addition, peptides with β-amino acids are more protease resistant and may form helical structures. By incorporating the β-amino acid at different positions in the peptide it is possible to achieve conformational variants of the same amino acid sequence, which allows the assessment of the best conformation for the desired biological activity.

Example 1B

Synthesis of Cyclic Peptides

The peptides described in Example 1 may also be synthesised using the following method:

Cyclic peptides such as P1 were synthesised according to Malesevic et al., 2004, published in Journal of Biotechnology 112, 73-77. Briefly, linear peptides were synthesized according to an Fmoc-protocol with Wang resin as a solid support. In a typical experiment, each peptide coupling is done twice with 1.5 eq. Fmoc-amino acid (0.3M in DMF*), 1.5 eq. TBTU (0.3M in DMF) and 3 eq. DIPEA (0.6M in DMF). After washing with DMF the Fmoc group is cleaved with a solution of 2% piperidine and 2% DBU in DMF. Wang resin is used as the solid support which is preloaded with Fmoc-Asp-ODmb attached to the resin via the side chain functionality. After assembly of the peptide sequence, the terminal protecting groups (Fmoc at the N-terminus, Dmb at the C-terminus) are cleaved from the linear precursor. A solution of 1.0-3.0 eq. (relative to resin loading) of HATU in 3 mL DMF followed by 6.0 eq. of DIPEA (relative to resin loading) is added to the resin. The reaction mixture is shaken for 45 min at room temperature and filtered. The cyclic peptide is cleaved from the resin and completely deprotected at the side chains using various cleavage cocktails: 95% TFA, 2.5% TIS, 2.5% $H_2O$ or 82.5 TFA, 5% phenol, 5% $H_2O$, 5% thioanisol, 2.5% EDT (reagent K) or 88% TFA, 5% phenol, 2% TIS, 5% $H_2O$ (reagent B). The cyclised and deprotected peptide is purified using preparative Reverse Phase-HPLC and has a purity of at least 98.5%. Molecular weight of each peptide as determined experimentally by mass spectrometry is shown in Table 1 below.

*Abbreviations are as follows: DIPEA, diisopropylethylamine; DMF, dimethyl formamide; Dmb, 2,4-dimethoxybenzyl; EDT, 1,2-ethanedithiol; Fmoc, Fluorenylmethoxycarbonyl; HATU, N[(dimethylamino)(1H-1,2,3-triazolo[4,5-b]pyridine-1-yl)methylene]-N-methylmethanaminium hexafluorophosphate N-oxide; HBTU, N-[(1H-benzotriazol-1-yl)(dimethylamino)methylene]-N-methylmethanaminium hexafluorophosphate N-oxide; HOAt, 7-aza-1,2,3-benzotriazol-1-ol; TBTU, N-[(1H-benzotriazol-1-yl)(dimethylamino)methylene]-N-methylmethanaminium tetrafluoroborate N-oxide; TFA, trifluoroacetic acid; TIS, triisopropylsilane.

Example 2

Inhibiting Cell Adhesion Mediated by ADAM8 DC Domain Using Cyclic Peptides

In this example, peptides synthesised as described in example 1 were used to target cell adhesion mediated by the ADAM8 DC domain. A recombinant DC domain of ADAM8 was expressed and purified from *E. coli* and then coated onto cell culture plates. Cells over-expressing ADAM8 were then allowed to bind to the ADAM8 DC domain on the plates.

96-well plates were coated with 50 µg/ml of recombinant ADAM8 DC protein in PBS at 4° C. for 16 h. To express the recombinant DC domain of ADAM8, the cDNA fragment encoding the A8 DC domain was generated by PCR using Platinum™ Pfx polymerase (Invitrogen) with the following primers: DCE-A8f, 5'-GGT GGC CCT GTG TGT GGA AAC-3' (SEQ ID NO:17); DCE-A8r, 5'-TAC ACA GTT GGG TGG TGC CCA-3' (SEQ ID NO:18). The resulting cDNA fragment was cloned into the bacterial expression vector pTrcHis2 (Invitrogen) containing a C-terminal Myc and His6 tag. This vector was transformed into *E. coli* strain TOP10 (Invitrogen). Recombinant protein expression was induced with 1 mM isopropyl-1-thio-D-galactopyranoside for 5 h to overnight. Purification of the recombinant DCE domain was done using the Xpress™ system protein purification kit (Invitrogen) according to the manufacturer's instructions for native protein preparations.

After application of the recombinant protein and blocking with bovine serum albumin for 1 h, $10^5$ cells in PBS or medium (with 5% FCS) were seeded onto the plates. For inhibition experiments, cells were incubated prior to seeding with peptides 1, 2, or 3 in various concentration ranging from 10 to 100 nM for 15 min at room temperature. After 1 h incubation at 37 C, the wells were rinsed 3× with PBS, and the remaining cells were quantified by counting 10 randomly chosen viewing fields (100-fold magnification). The 100% value of cell adhesion was obtained by allowing $10^5$ cells to adhere completely. Values are given as percentage of the total number of attached cells.

A significant number of cells bound to the coated plates, but only those cells showing over-expression of ADAM8. This indicates a homophilic interaction between the ADAM8 DC domains coated on the plates and the cell-bound DC domains.

Figure 8:
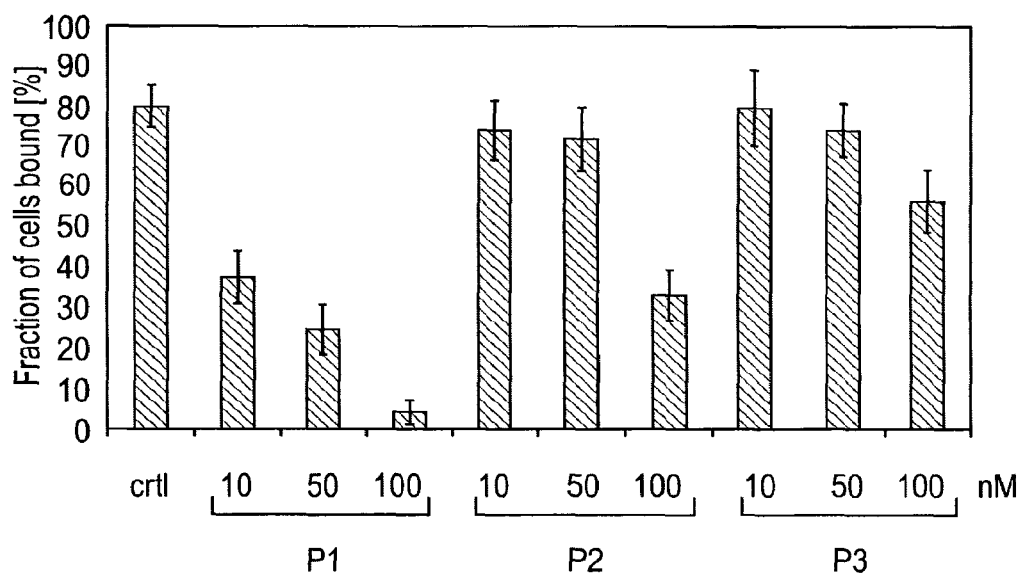
FIG. 8 shows inhibition of cell adhesion by cyclic peptides P1, P2, and P3. Cells expressing ADAM8 were seeded onto wells coated with the 50 µg/ml of the recombinant ADAM8 disintegrin/cysteine-rich (DC) domain. Peptides were preincubated with the cells 1 hour prior to seeding. The numbers of remaining cells were counted after extensive washing with phosphate buffered saline.

Cyclic peptides that presented the 3 amino acid motif in different conformations were tested for their ability to block the ADAM8 DC interaction, as shown in FIG. 8. P1 was very potent in the inhibition of cell adhesion and the concentration used was in the range of 10 nM. These results indicate that cyclic peptides can mimic the integrin binding loop motif and that targeting the 3 amino acid motif is sufficient to suppress cell adhesion mediated by ADAM8. Inhibition of the ADAM8 DC domain homophilic interaction involved in cell adhesion is also indicative of inhibition of the catalytic activity of ADAM8, since the DC domain is involved in the formation of ADAM8 multimers which are required for proteolytic activity in vivo.

Example 3

Inhibition of Recombinant ADAM8 Using Cyclic Peptides

In the following example, the ability of cyclic peptides to inhibit the activity of a recombinant ADAM8 was tested in fluorescence assays using a fluorogenic ADAM8 substrate (Moss and Rasmussen, 2007).

Activity of purified recombinant ADAM8 was assessed by using a fluorogenic CD23 peptide (Dabcyl-HGDQ-MAQKSK(5-FAM)-CONH$_2$, SEQ ID NO:19) as a substrate. 50 ng substrate was incubated with 100 ng of ADAM8 in assay buffer (25 mM TrisHCl pH 7.5, 10 mM CaCl$_2$, 150 mM NaCl) at 37° C. in the time range of 0 to 18 hours. Potential ADAM8 inhibitors were preincubated for 30 min before addition of the substrate. As a negative control, CD23 was incubated with assay buffer. For determination of ADAM10 activity, 100 ng of the recombinant ADAM10 protein (R&D systems) was used in conjunction with the fluorogenic substrate Dabcyl-LAQA(HomoPhe) RSC (Fluorescein)-NH$_2$ (SEQ ID NO:55) in assay buffer (TrisHCl pH 9.0, 2.5 µM ZnCl$_2$). For both assays the final volume in each well was 150 µl. Activity was measured as increase in fluorescence resulting from ADAM8/ADAM10 to cleave the quenched fluorescent substrates (λ excitation: 485 nm; λ emission: 520 nm) using a BMG Optima plate reader fluorometer.

Figure 1B:
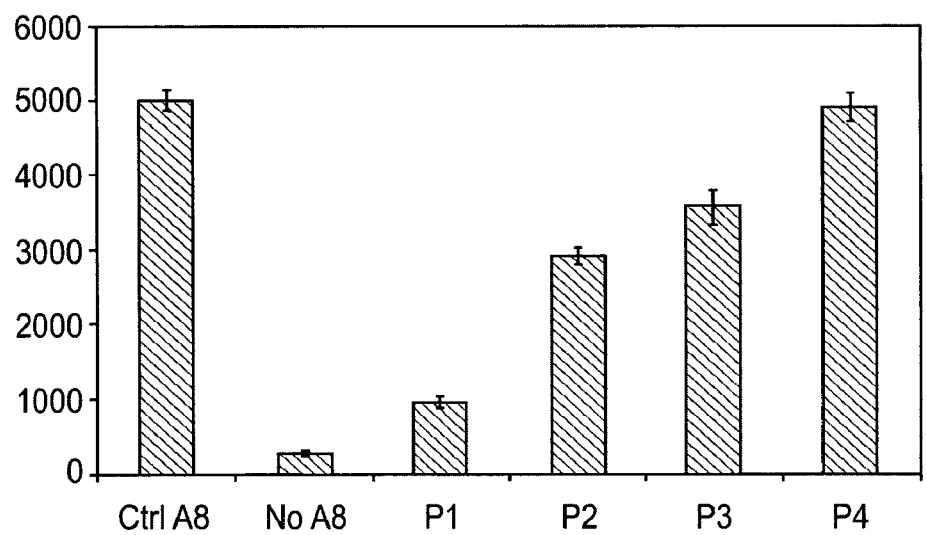
FIG. 1B shows the inhibition of ADAM8 activity in the presence of peptide inhibitors (whose structure is shown in FIG. 5) comprising a KDK motif which is found in the ADAM8 integrin binding loop structure. Cyclic peptides P1 to P3 differ in terms of their 3D structure in view of a difference in the position of a β-amino acid, whereas P4 represents the same sequence in a linear conformation. All peptides were used at a concentration of 100 nM. Assays were performed as described below using CD23 as the substrate.
Figure 1C:
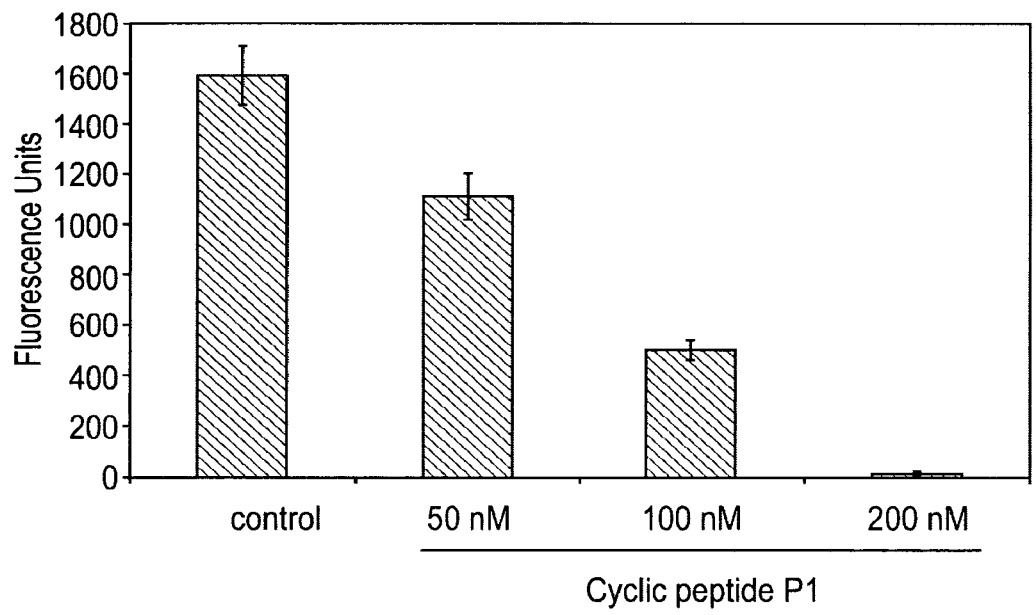
FIG. 1C shows the inhibition of ADAM8 activity by cyclic peptide P1 when used in the concentration range of 50-200 nM. Assays were performed as described below using CD23 as the substrate.
Figure 2:
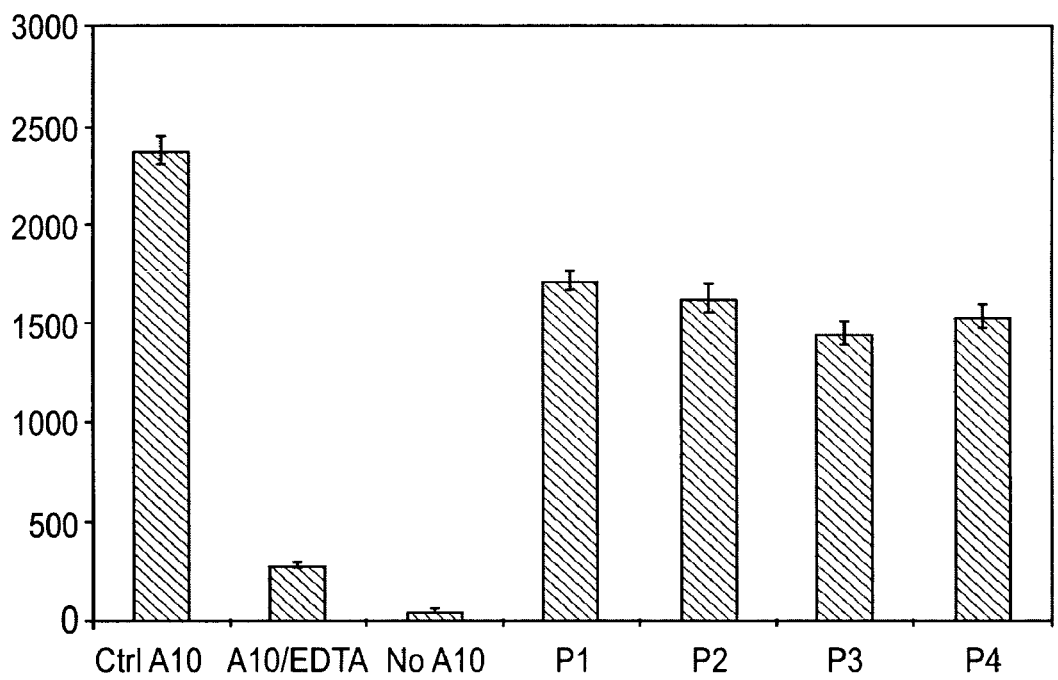
FIG. 2 shows the effect of peptides P1-P4 on the activity of ADAM10 (A10) at a concentration of 100 nM, respectively. Assays were performed as described below using the LAQA peptide as a substrate for ADAM10.

The results are shown in FIGS. 1B, 1C & 2. FIG. 1B indicates that the linear peptide P4 had little effect on ADAM8 activity. Cyclic peptides P2 and P3 showed inhibition of ADAM8 proteolytic activity but cyclic peptide P1 showed the most marked inhibition. FIG. 2 shows that none of the peptides P1 to P4 was a good inhibitor of ADAM10.

FIG. 1C shows the concentration-dependant inhibition of ADAM8 by cyclic peptide P1.

The results support the notion that the cyclic peptides inhibit ADAM8 activity even when the substrate is a small molecule. In vivo substrates are membrane proteins so their steric requirement would be much bigger, which would argue for a more pronounced effect of the DC domain on the efficiency of cleavage. Surprisingly, one out of a selection of peptides (P1) was able to markedly reduce ADAM8 catalytic activity, even though the substrate used was a small peptide. Peptide P1 selectively inhibited ADAM8 with an $IC_{50}$ value of about 50 nM, but showed little inhibition of ADAM10.

TABLE 1

List of peptides used to inhibit ADAM8 (compare alignment of mouse ADAM protease). Note that in the peptides P5, P6, and P7, the individual amino acids of the KDK motif have been replaced by an alanine, which abolishes the inhibitory properties of the peptides. P4 is the linear variant of the cyclic peptides P1, P2, and P3.

| Peptide | Nr. | Theoretical molar weight (g/mol) | Mw (as determined by mass spectrometry) | A8 Inhibition | SEQ ID NO |
|---|---|---|---|---|---|
| c(RLsKDK) | P1 | 727.43 | 726.96 | +++; IC50 100 nM | 49 |
| c(rLSKDK) | P2 | 727.43 | 727.21 | +; IC50: >500 nM | 56 |
| c(R1SKDK) | P3 | 727.43 | 726.98 | +; IC50 >500 nM | 57 |
| H-RLSKDK-OH | P4 | 745.94 | 746.02 | — | 3 |
| c(RLsADK) | P5 | 662.40 | 662.30 | — | 58 |
| c(RLsKAK) | P6 | 680.65 | 680.30 | — | 59 |
| c(RLsKDA) | P7 | 662.40 | 662.12 | — | 60 |

Example 4

Inhibition of ADAM8-Mediated CD23 Release from Cells by Cyclic Peptides

The ability of the cyclic peptide P1 to inhibit ADAM8-mediated shedding of CD23 from RPMI 8866 cells was measured using an ELISA.

Cells of the human B cell line RPMI 8866 were seeded out in 12-well plates at a density of $2 \times 10^5$/well with or without TIMP-1 (inhibitor of ADAM10), ADAM10 prodomain (specific inhibitor of ADAM10) or peptide inhibitors for 6 hours. After 6 hours, the amounts of CD23 released in the supernatants were determined by a sCD23-monoclonal antibody coated ELISA (Bender Med Systems). The standards were prepared as eight serial 1:2 dilutions ranging from 400 to 12.5 units/ml. Blank and samples duplicates (100 µl) were also applied, after that 50 µl of diluted biotinylated anti-CD23 monoclonal antibody (1:100) was added. After the application of all required solutions the plate was incubated for 2 hours at room temperature. The multiwell plate was then emptied and washed 4 times with washing buffer to remove the unbound biotin conjugates and re-incubated with 100 µl/well of diluted streptavidin-HRP (1:100) for 1 hr at room temperature. After additional washing of the plate, TMB substrate solution (100 µl/well) was added for 10-20 min until colour developed. Absorbance in each individual well was determined using an ELISA plate reader at 405 nm.

Figure 3:
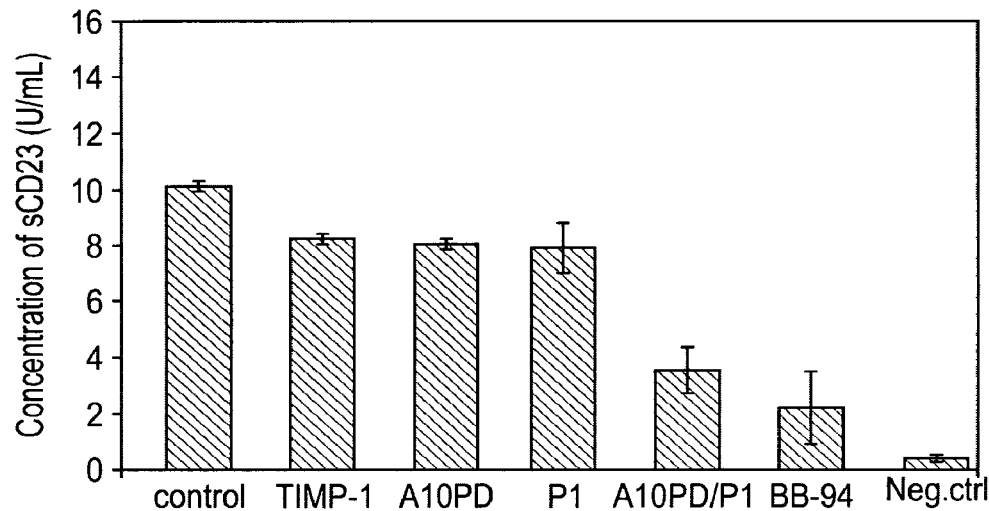
FIG. 3 shows the inhibition of CD23 release from RPMI 8866 cells by cyclic peptide P1 as measured by ELISA. Cells were incubated with for 6 hours with TIMP-1 (500 nM), ADAM10 prodomain (A10PD, 10 µg/ml), P1 (200 nM), and batimastat (200 nM). The control used was supernatant from RPMI 8866 cells under culture conditions.

The results are shown in FIG. 3. The amount of soluble CD23 released from RPMI 8866 cells when using the P1 peptide is reduced to an extent that reflects the contribution of ADAM8 to the overall cleavage of CD23 in these cells (Fourie et al., 2003). In these experiments, ADAM10 as a principal sheddase of CD23 was inhibited by either TIMP-1 (Tissue Inhibitor of Metalloprotease) or, even more specific, the ADAM10 prodomain (Moss et al., in press). When the ADAM10 prodomain and P1 were used in conjunction, an additive effect on the CD23 release was observed, arguing that both ADAMs are contributing to more than 60% of the CD23 release from these cells.

Example 5

Inhibition of ADAM8-Mediated Cell Migration Through an Artificial Extracellular Matrix by Cyclic Peptide In this example, the ability of cyclic peptide to inhibit ADAM8 mediated tumour cell migration through an artificial extracellular matrix (Matrigel®) was measured in a cell invasion assay. Rat glioma C6 cells were stably transfected with full length ADAM8 cDNA [Schlomann et al, 2002]. Untransfected C6 glioma cells served as controls. $5 \times 10^4$ cells were suspended in 100 µl of culture medium in the absence or presence of peptides (100 nM) and loaded into Matrigel invasion chambers (BD Biosciences, Heidelberg, Germany), which were handled according to the supplier's manual. After 20 hours incubation time, invaded cells were fixed with methanol, stained with toluidine blue, and counted. Experiments were performed in triplets and from each well, 10 viewing fields were counted manually under the microscope. Differences between the values obtained were analysed using the Mann-Whitney U test.

Figure 4:
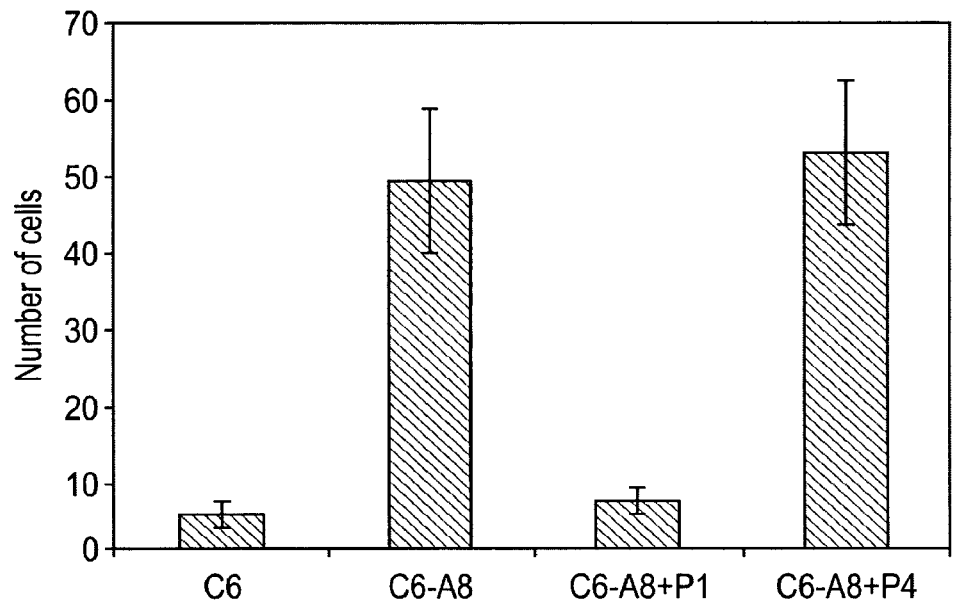
FIG. 4 shows the results of a cell invasion assay using glioma (invasive brain tumour) cells overexpressing mouse ADAM8 in the absence and presence of the cyclic peptide P1 and linear peptide P4. Peptides in a concentration of 200 nM were preincubated with the cells 1 hour prior to seeding on the invasion chambers. Values were given as the mean of 30 viewing fields from 3 independent plates.

The results are shown in FIG. 4. Peptide P1 dramatically reduced tumour cell invasion in ADAM8 expressing cells. This demonstrates the enormous potency of this compound to inhibit ADAM8 mediated cell migration, which is important in malignancy for brain tumours (Wildeboer et al., 2006) as well as in prostate, lung, kidney and pancreas tumours.

Various modifications of the invention in addition to those shown and described herein will be apparent to the skilled person from the foregoing description and fall within the scope of the appended claims. All patent and literature references cited in the present specification are hereby incorporated by reference in their entirety.

Example 6

Test for Specificity of the Peptide Inhibitor P1

Specificity of the ADAM8 inhibitor peptide P1 was tested against other active ADAM proteases, for which recombinant proteins containing the disintegrin domain exist. The 1050 values for these ADAM proteins are shown in table 2. The maximal concentration of the inhibitor peptide was 10 µM.

| ADAM protease | Substrate used | ADAM inhibition with P1 |
|---|---|---|
| ADAM8 | CD23* | $IC_{50}$: 100 nM |
| ADAM9 | TNF peptide* | No inh. at 10 µM |
| ADAM10 | LAQA* (SEQ ID NO: 61) | No inh. at 10 µM |
| ADAM12 | LAQA* (SEQ ID NO: 61) | No inh. at 10 µM |
| ADAM17 (TACE) | LAQA* (SEQ ID NO: 61) | No inh. at 10 µM |

*substrates used in these assays, e.g. as described in (Moss and Rasmussen, 2007):
CD23: Dabcyl-HGDQMAQKSK(5-FAM)-CONH$_2$ (SEQ ID NO: 19)
TNF peptide: Dabcyl-SPLAQAVRSK(Fam)-NH$_2$ (SEQ ID NO: 21)
LAQA: Dabcyl-LAQAHomophe-RSK(Fam)-NH$_2$ (SEQ ID NO: 20)

ADAM catalytic/disintegrin constructs were monitored at 5-min intervals using the indicated fluorescent substrates with excitation and emission wavelengths of 485 and 530 nm, respectively. The substrates were diluted from a 10 mM stock in DMSO to 10 μM in assay buffer containing 20 mM Tris, pH 8.0, and 6×10$^{-4}$% Brij-35. For experiments with ADAM8 only, 10 mM CaCl$_2$ was added to the buffer. Reactions were run in a 96-well plate with either inhibitor (10 nM-10 μM) in 1% DMSO or a 1% DMSO control. Background wells contained substrate and 1% DMSO and were subtracted from all other wells. Endpoints were determined in wells containing substrate and an excess of ADAM17 for the TNF-alpha substrate and ADAM8 for the CD23 substrate. Concentrations of ADAM proteins were in the range of 2.0 nM for TACE, 10 nM for ADAMS, 5 nM for ADAM10, 10 nM for ADAM8, and 2 nM for ADAM12.

These data demonstrate that the peptide inhibitor P1 (c(RLsKDK) (SEQ ID NO: 49) is highly specific for ADAM8 and does not inhibit any of the other catalytically active ADAMs tested even in high concentrations such as 10 μM.

Example 7

Test of Inhibitor P1 in Preventing Invasion of ADAM8$^+$ Cells by Blocking ADAM8 Activation ADAM8 was overexpressed by transfection in fibroblast (L929) and glioma (C6) cell lines which show no invasive potential under untransfected conditions. When ADAM8 expressing plasmids were transfected into these cell lines, the cells became highly invasive in Matrigel Invasion assays (e.g. as described in example 5). No invasion compared to control (vector without ADAM8) was observed in the inactive variant containing an E to Q mutation at amino acid position 330 of the active site. Invasion is also mediated by a soluble variant of ADAM8, which is released upon activation of ADAM8 in these cells.

Figure 10:
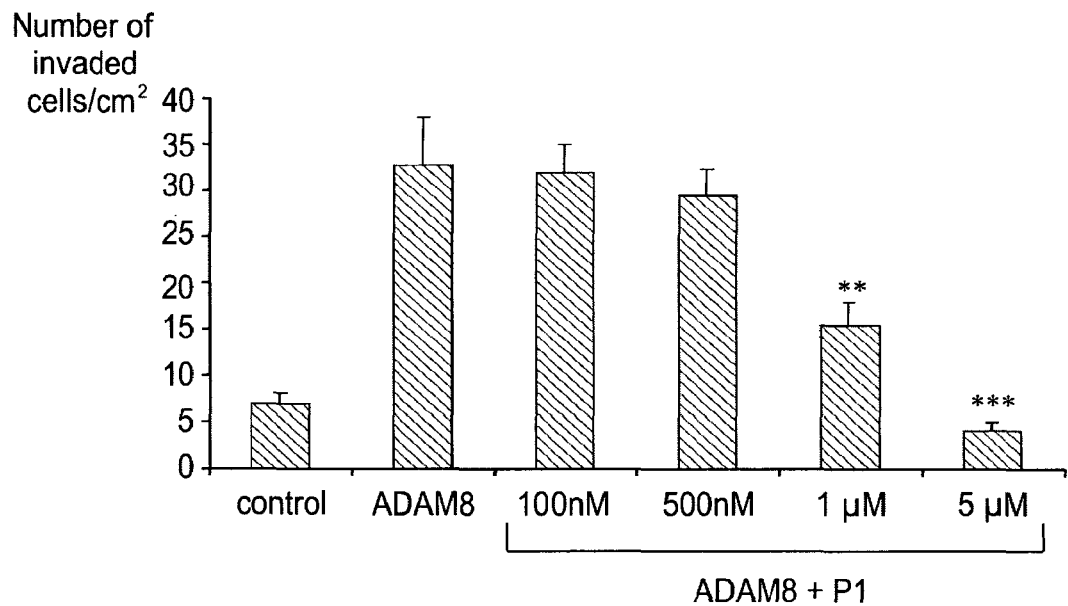
FIG. 10 shows C6 glioma cell invasiveness induced by ADAM8 overexpression, and its dose-dependent inhibition by cyclic peptide P1, in a Matrigel invasion assay. Statistical significance:  indicates P<0.01, * indicates P<0.001.

Inhibitory peptide P1 blocks cell invasion in a dose-dependent manner in C6 glioma cells (FIG. 10). The optimal concentration of P1 was assessed for complete inhibition of cell invasion.

Figure 11:
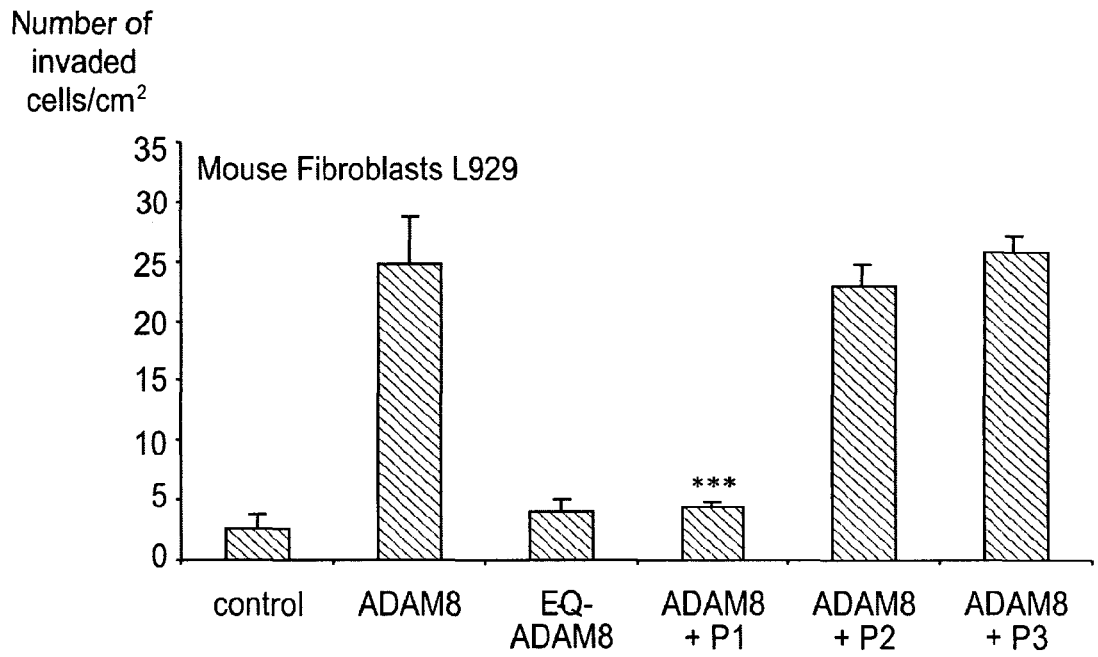
FIG. 11 shows the effect on ADAM-8 mediated cell invasion of mouse fibroblast (L929) cells of cyclic peptides P1, P2 and P3, in a Matrigel invasion assay. Peptides were applied in a concentration of 5 µM. As a negative control, no invasion was observed in mutant cells expressing an inactive ADAM-8 (EQ-ADAM8). Statistical significance: *** indicates P<0.001.
Figure 12:
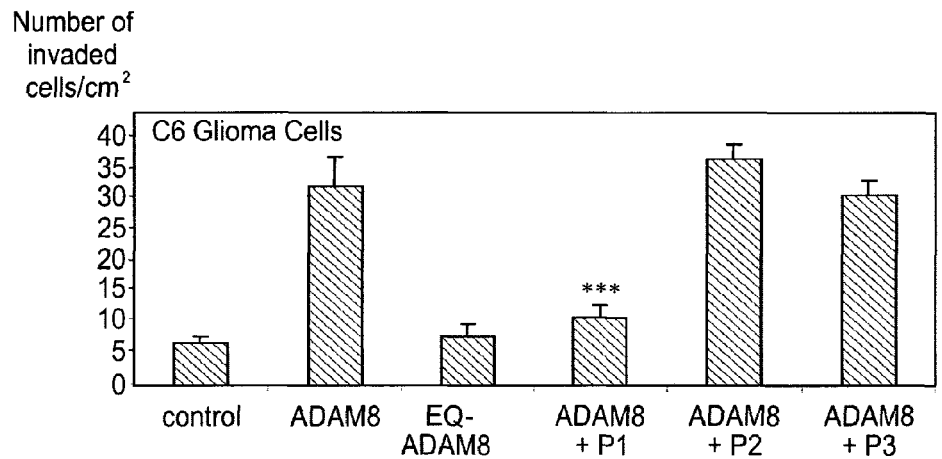
FIG. 12 shows the effect on ADAM-8 mediated cell invasion of C6 glioma cells of cyclic peptides P1, P2 and P3, in a Matrigel invasion assay. Peptides were applied in a concentration of 5 µM. As a negative control, no invasion was observed in mutant cells expressing an inactive ADAM-8 (EQ-ADAM8). Statistical significance: *** indicates P<0.001.

The inhibitory peptide P1 blocks the proteolytic release of ADAM8 into a soluble form, which is necessary to mediate cell invasion. P1 blocks ADAM8 activation leading to a reduced cell invasion. Cell-based assays were used to assess the potential of peptide P1 to block cell invasion. These results demonstrate that due to a lack of proper processing of ADAM8, the invasion of otherwise invasive cell types was significantly blocked (FIGS. 11 and 12).

Example 8

Toxicological Studies with Cyclic Peptides P1, P2, and P3

Figure 13:
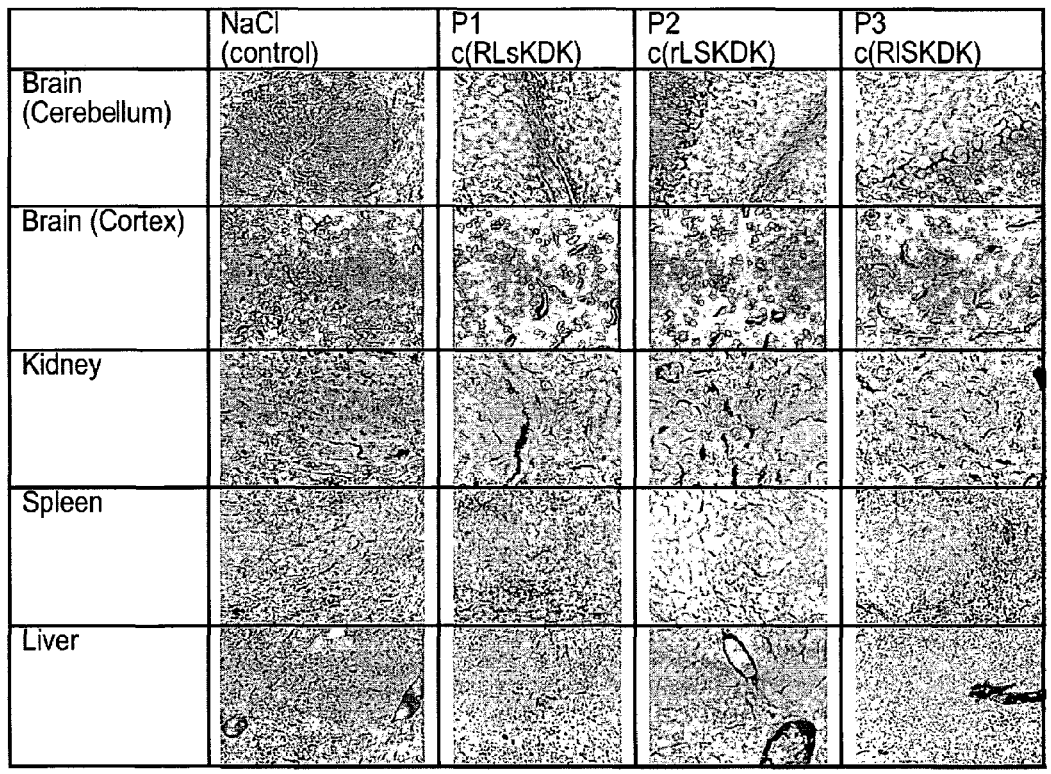
FIG. 13 shows that none of cyclic peptides P1, P2 and P3 were cytotoxic in mice. After four weeks of treatment with P1, P2 and P3, or NaCl (control), mice were sacrificed and representative organs were dissected and assessed histologically by normal hematoxylin/eosin (HE) staining. For each cohort of mice, one representative was documented for brain (cerebellum and cortex), liver, spleen, and kidney. Histological studies did not show any evidence of toxicity for any of the cyclic peptides.

The three peptide variants with similar sequences but different conformations (P1, P2, and P3) were tested for toxicity in mice. To test for acute and for chronic toxicity, we used dosages of 1 μg, 5 μg, and 10 μg per gram of body weight in 100 μl of injection volume. Mice (strain C57BL/6) were either injected once (acute toxicity) or weekly three-times (chronic toxicity) intraperitoneal with the dosages indicated. All mice were analysed in cohorts of n=6, and NaCl injected mice were used as controls. After 4 weeks observation time, all mice were alive and did not show any obvious abnormalities. We assessed spontaneous behaviour and motor performance of the mice. For both types of analyses, we were not able to detect any differences in behaviour. After 4 weeks, mice were sacrificed and representative organs were dissected and assessed histologically by normal hematoxylin/eosin (HE) staining. For each cohort of mice, one representative is documented for brain (cerebellum and cortex), liver, spleen, and kidney in FIG. 13. These histological studies did not show any evidence of toxicity of any of the cyclic peptides.

REFERENCES

Amour, A., Knight, C. G., Webster, A., Slocombe, P. M., Stephens, P. E., Knäuper, V., Docherty, A. J. P. & Murphy, G. The in vitro activity of ADAM-10 is inhibited by TIMP-1 and TIMP-3. FEBS Lett (2000) 473, 275-279.

Aumailley, M., Gurrath, M., Müller, G., Calvete, J., Timpl, R., Kessler, H. (1991) Arg-Gly-Asp constrained within cyclic pentapeptides. Strong and selective inhibitors of cell adhesion to vitronectin and laminin fragment P1. FEBS Letters 291, 50-54.

Blobel CP. ADAMs: key components in EGFR signalling and development. Nat Rev Mol Cell Biol 6: 32-43, 2005

Bridges, L. C., Hanson, K. R., Tani, P. H., Mather, T., Bowditch, R. D. (2003) Integrin alpha4beta1-dependent adhesion to ADAM28 (MDC-L) requires an extended surface of the disintegrin domain. Biochemistry 42:3734-41.

Fourie, A. M, Coles, F., Moreno, V., Karlsson, L. (2003) Catalytic activity of ADAM8, ADAM15, and MDC-L (ADAM28) on synthetic peptide substrates and in ectodomain cleavage of CD23. J Biol Chem 278:30469-77.

Kelly, K., Hutchinson, G., Nebenius-Oosthuizen, D., Smith, A. J., Bartsch, J. W., Horiuchi, K., Rittger, A., Manova, K., Docherty, A. J., Blobel, C. P. (2005) Metalloprotease-Disintegrin ADAM8: expression analysis and targeted deletion in mice. Developmental Dynamics, 232, 221-231.

King, N. E., Zimmermann, N., Pope, S. M., Fulkerson, P. C., Nikolaidis, N. M., Mishra, A., Witte, D. P. and Rothenberg, M. E. (2004); Expression and Regulation of a Disintegrin and Metalloproteinase (ADAM) 8 in Experimental Asthma; Am. J. Respir. Cell Mol. Biol.; 31(3): 257-265.

Marti, R. E., Bleicher, K. H., Bair, K. W. (1997) Solid Phase Synthesis of b-peptides via Arndt-Eistert homologation of Fmoc-protected Amino Acid Diazoketones. Tetrahedron Letters 38, 6145-6148.

Moss, M., Bartsch, J. W. (2004) Therapeutic benefits from targeting of ADAM family members. Biochemistry 43, 7227-35.

Moss M. L., Rasmussen, F. H. (2007) Fluorescent substrates for the proteinases ADAM17, ADAM10, ADAM8, and ADAM12 useful for high-throughput inhibitor screening. Anal Biochem 366:144-148.

Naus, S., Richter, M., Wildeboer, D., Schachner, M., Moss, M., Bartsch, J. W. (2004) Ectodomain shedding of the neural recognition molecule CHL1 by the metalloprotease-disintegrin ADAM8 promotes neurite outgrowth and suppresses neuronal cell death. J. Biol. Chem. 279, 16083-16090.

Naus, S., Reipschlager, S., Wildeboer, D., Lichtenthaler, S., Moss, M., Bartsch, J. W. (2006) Identification of novel substrates for the Metalloprotease-Disintegrin ADAM8. Biological Chemistry 387, 337-346

J. J. Peschon, J. L. Slack, P. Reddy, K. L. Stocking, S. W. Sunnarborg, D. C. Lee, W. E. Russell, B. J. Castner, R. S. Johnson, J. N. Fitzner, R. W. Boyce, N. Nelson, C. J. Kozlosky, M. F. Wolfson, C. T. Rauch, D. P. Cerretti, R. J. Paxton, C. J. March, and R. A. Black. An Essential Role for Ectodomain Shedding in Mammalian Development. Science, (1998): 282(5392): 1281-1284

Schlomann, U., Wildeboer, D., Webster, A., Antropova, O., Zeuschner, D., Docherty, A. J., McLoughlin, S., Skelton, L., Jockusch, H., Bartsch, J. W. (2002) The Metalloprotease-Disintegrin ADAM8: Processing by autocatalysis is required for proteolytic activity and cell adhesion. J. Biol. Chem 277, 48210-48219.

Schlomann, U., Rathke-Hartlieb, S., Yamamoto, S., Jockusch, H., and Bartsch, J. W. (2000). Tumor necrosis factor (TNF) alpha induces a metalloprotease-disintegrin, ADAM8 (CD 156): Implications for neuron-glia interactions during neurodegeneration. J. Neurosci. 20, 7964-7971.

Seals, D. F. & Courtneidge, S. A. The ADAMs family of metalloproteases: multidomain proteins with multiple functions. Genes Dev (2003) 17, 7-30.

Wildeboer, D., Naus, S., Sang, Q. X., Bartsch, J. W., Pagenstecher, A. (2006) Expression levels and activities of human Metalloproteinase-disintegrins ADAM8 and ADAM19 in primary brain tumors are associated with invasive activity. J Neuropath Exp Neurol 65, 516-527.

Xiong, J. P., Stehle, T., Zhang, R., Joachimiak, A., Frech, M., Goodman, S. L., Arnaout, M. A. (2002). Crystal structure of the extracellular segment of integrin alpha Vbeta3 in complex with an Arg-Gly-Asp ligand. Science 296:151-155.

Yoshida, S., Setoguchi, M., Higuchi, Y., Akizuki, S., and Yamamoto, S. (1990) Molecular cloning of cDNA encoding MS2 antigen, a novel cell surface antigen strongly expressed in murine monocytic lineage. Int. Immunol. 2, 585-591

Zhao, Y. G., Wei, P., Sang, Q. X. (2001) Inhibitory antibodies against endopeptidase activity of human adamalysin 19. Biochem Biophys Res Commun. 289:288-294.

---

The invention claimed is:

1. A cyclic peptide of formula I:

(I)

wherein $X^0$, $X^1$, $X^2$, and $X^3$ each independently represents an amino acid residue;

wherein each amino acid residue in the cyclic peptide is joined by a peptide bond;

wherein each $X^0$ may be the same or different;

wherein $X^1$, $X^2$, and $X^3$ are selected such that the cyclic peptide comprises one of the following amino acid sequences: KDM, ARQ, DSD, NAT, VRQ, and TDD; and wherein n is 0 to 4;

or a pharmaceutically acceptable salt thereof.

2. The cyclic peptide according to claim 1, wherein the cyclic peptide has the formula II:

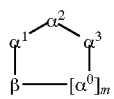

(II)

wherein $\alpha^0$, $\alpha^1$, $\alpha^2$ and $\alpha^3$ each independently represents an alpha-amino acid residue;

wherein each $\alpha^0$ may be the same or different;

wherein D represents a D-amino acid residue;

wherein each amino acid residue in the cyclic peptide is joined by a peptide bond;

wherein m is 1 to 3; and wherein $\alpha^1$, $\alpha^2$ and $\alpha^3$ are selected such that the cyclic peptide comprises one of the following amino acid sequences: KDM, TSE, ARQ, DSD, NAT, VRQ, and TDD;

or a pharmaceutically acceptable salt thereof.

3. The cyclic peptide according to claim 2, wherein the cyclic peptide has the formula III:

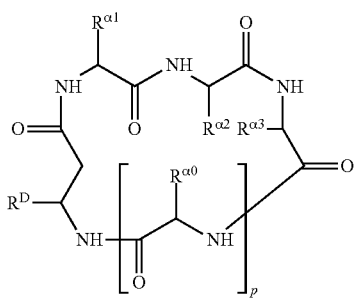

(III)

wherein $R^{\alpha 0}$, $R^{\alpha 1}$, $R^{\alpha 2}$ and $R^{\alpha 3}$ each independently represents an alpha-amino acid side-chain;

wherein each $R^{\alpha 0}$ may be the same or different;

wherein $R^D$ represents a D amino acid side-chain;

wherein p is 1 to 3; and wherein $R^{\alpha 1}$, $R^{\alpha 2}$ and $R^{\alpha 3}$ are selected such that the cyclic peptide comprises one of the following amino acid sequence: KDM, TSE, ARQ, DSD, NAT, VRQ, and TDD;

or a pharmaceutically acceptable salt thereof.

4. The cyclic peptide according to claim 1, wherein the cyclic peptide comprises a sequence KDM.

5. The cyclic peptide according to claim 1, wherein n, $X^0$, $X^1$, $X^2$, and $X^3$ are selected such that the cyclic peptide comprises one of the following amino acid sequences: RPKKDM (SEQ ID NO: 2), REQARQ (SEQ ID NO: 8), RDDSD (SEQ ID NO: 10), QEAINAT (SEQ ID NO: 11), REQVRQ (SEQ ID NO: 14), and RPPTDD (SEQ ID NO: 16).

6. The cyclic peptide according to claim 5, wherein the cyclic peptide comprises a sequence RPKKDM (SEQ ID NO: 2).

7. The cyclic peptide according to claim 1, which is cyclo(RGkTSE), cyclo(RPkKDM), cyclo(REqARQ), cyclo(RdDSD), cyclo(QEAiNAT), cyclo(REqVRQ), or cyclo(R-PpTDD), wherein a lower case letter represents a D amino acid and an upper case letter represents an alpha amino acid, or a pharmaceutically acceptable salt thereof.

8. The cyclic peptide according to claim 7, which is cyclo(Arg-Pro-{D-Lys}-Lys-Asp-Met) or a pharmaceutically acceptable salt thereof.

9. A composition comprising the cyclic peptide as set out in claim 1, or a pharmaceutically acceptable salt thereof, and a pharmaceutically acceptable excipient.

10. A cyclic peptide of formula I:

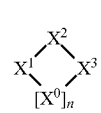

(I)

wherein $X^0$, $X^1$, $X^2$ and $X^3$ each independently represents an amino acid residue;

wherein each amino acid residue in the cyclic peptide is joined by a peptide bond;

wherein each $X^0$ may be the same or different;

wherein $X^0$, $X^1$, $X^2$ and $X^3$ are selected such that the cyclic peptide comprises an amino acid sequence RPTRGD (SEQ ID NO: 6);

and wherein n is 3 or 4;

or a pharmaceutically acceptable salt thereof.

11. A cyclic peptide which is cyclo(RPtRGD), wherein a lower case letter represents a D amino acid and an upper case letter represents an alpha amino acid, or a pharmaceutically acceptable salt thereof.

12. A cyclic peptide of formula II:

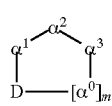
(II)

wherein $\alpha^0$, $\alpha^1$, $\alpha^2$ and $\alpha^3$ each independently represents an alpha-amino acid residue;
wherein each $\alpha^0$ may be the same or different;
wherein D represents a D-amino acid residue;
wherein each amino acid residue in the cyclic peptide is joined by a peptide bond;
wherein m is 1 to 3; and
wherein $\alpha^1$, $\alpha^2$ and $\alpha^3$ are selected such that the cyclic peptide comprises one of the following amino acid sequences: KDM, TSE, KDE, SNS, ARQ, MGD, DSD, NAT, VRQ, ATD and TDD;
or a pharmaceutically acceptable salt thereof.

13. The cyclic peptide according to claim 12, wherein the cyclic peptide has the formula III:

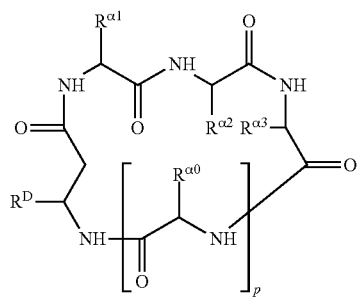
(III)

wherein $R^{\alpha 0}$, $R^{\alpha 1}$, $R^{\alpha 2}$, and $R^{\alpha 3}$, each independently represents an alpha-amino acid side-chain;
wherein each $R^{\alpha 0}$ may be the same or different;
wherein $R^D$ represents a D-amino acid side-chain;
wherein p is 1 to 3; and
wherein $R^{+1}$, $R^{\alpha 2}$, and $R^{\alpha 3}$ are selected such that the cyclic peptide comprises one of the following amino acid sequences: KDM, TSE, KDE, SNS, ARQ, MGD, DSD, NAT, VRQ, ATD and TDD;
or a pharmaceutically acceptable salt thereof.

14. A cyclic peptide of formula I:

(I)

wherein $X^0$, $X^1$, $X^2$, and $X^3$ each independently represents an amino acid residue;
wherein each amino acid residue in the cyclic peptide is joined by a peptide bond;
wherein each $X^0$ may be the same or different;
$X^1$, $X^2$, and $X^3$ are selected such that the cyclic peptide comprises one of the following amino acid sequences: RPKKDM (SEQ ID NO:2), RPAKDE (SEQ ID NO: 5), REQARQ (SEQ ID NO: 8), RQAMGD (SEQ ID NO: 9), RDDSD (SEQ ID NO: 10), QEAINAT (SEQ ID NO: 11), RAAKDE (SEQ ID NO: 12), RGSSNS (SEQ ID NO: 13), REQVRQ (SEQ ID NO: 14), RPAATD (SEQ ID NO: 15), and RPPTDD (SEQ ID NO: 16); and
wherein n is 3 or 4;
or a pharmaceutically acceptable salt thereof.

15. A cyclic peptide which is cyclo(RGkTSE), cyclo(RPaKDE), cyclo(RPkKDM), cyclo(RDsSNS), cyclo(REqARQ), cyclo(RQaMGD), cyclo(RdDSD), cyclo(QEAiNAT), cyclo(RAaKDE), cyclo(RGsSNS), cyclo(REqVRQ), cyclo(RPaATD), or cyclo(RPpTDD), wherein a lower case letter represents a D-amino acid residue and an upper case letter represents an alpha amino acid residue, or a pharmaceutically acceptable salt thereof.

16. The cyclic peptide according to claim 15 which is cyclo(Arg-Pro-{D-Lys}-Lys-Asp-Met), or a pharmaceutically acceptable salt thereof.

* * * * *

SEQUENCE LISTING

```
<160> NUMBER OF SEQ ID NOS: 61

<210> SEQ ID NO 1
<211> LENGTH: 13
<212> TYPE: PRT
<213> ORGANISM: Artificial Sequence
<220> FEATURE:
<223> OTHER INFORMATION: Catalytic consensus sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 1

His Glu Xaa Xaa His His Xaa Xaa Gly Xaa Xaa His Asp
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined

<400> SEQUENCE: 2

Arg Pro Lys Lys Asp Met
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
```

```
<400> SEQUENCE: 3

Arg Leu Ser Lys Asp Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined

<400> SEQUENCE: 4

Arg Gly Lys Thr Ser Glu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined

<400> SEQUENCE: 5

Arg Pro Ala Lys Asp Glu
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined

<400> SEQUENCE: 6

Arg Pro Thr Arg Gly Asp
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined

<400> SEQUENCE: 7

Arg Asp Ser Ser Asn Ser
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 8

Arg Glu Gln Ala Arg Gln
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 9

Arg Gln Ala Met Gly Asp
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 10

Arg Asp Asp Ser Asp
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 11

Gln Glu Ala Ile Asn Ala Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined
```

```
<400> SEQUENCE: 12

Arg Ala Ala Lys Asp Glu
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 13

Arg Gly Ser Ser Asn Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 14

Arg Glu Gln Val Arg Gln
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 15

Arg Pro Ala Ala Thr Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Synthetic peptide is cyclic with terminal amino
      acids joined

<400> SEQUENCE: 16

Arg Pro Pro Thr Asp Asp
1               5

<210> SEQ ID NO 17
<211> LENGTH: 21
<212> TYPE: DNA
<213> ORGANISM: Artificial Sequence
```

-continued

```
<220> FEATURE:
<223> OTHER INFORMATION: Primer

<400> SEQUENCE: 17
ggtggccctg tgtgtggaaa c                                                    21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
tacacagttg ggtggtgccc a                                                    21

<210> SEQ ID NO 19
<211> LENGTH: 10
<212> TYPE: PRT
<213> ORGANISM: Artificial Sequence
<220> FEATURE:
<223> OTHER INFORMATION: Fluorogenic CD23 peptide

<400> SEQUENCE: 19

His Gly Asp Gln Met Ala Gln Lys Ser Lys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Fluorogenic substrate
<220> FEATURE:
<221> NAME/KEY: MOD_RES
<222> LOCATION: (5)..(5)
<223> OTHER INFORMATION: Xaa is homophenylalanine

<400> SEQUENCE: 20

Leu Ala Gln Ala Xaa Arg Ser Lys
1               5

<210> SEQ ID NO 21
<211> LENGTH: 10
<212> TYPE: PRT
<213> ORGANISM: Artificial Sequence
<220> FEATURE:
<223> OTHER INFORMATION: TNF peptide substrate

<400> SEQUENCE: 21

Ser Pro Leu Ala Gln Ala Val Arg Ser Lys
1               5                   10

<210> SEQ ID NO 22
<211> LENGTH: 76
<212> TYPE: PRT
<213> ORGANISM: Homo sapiens

<400> SEQUENCE: 22

Asp Ala Gly Glu Glu Cys Asp Cys Gly Thr Pro Lys Glu Cys Glu Leu
1               5                   10                  15

Asp Pro Cys Cys Glu Gly Ser Thr Cys Lys Leu Lys Ser Phe Ala Glu
                20                  25                  30

Cys Ala Tyr Gly Asp Cys Cys Lys Asp Cys Arg Phe Leu Pro Gly Gly
        35                  40                  45
```

```
Thr Leu Cys Arg Gly Lys Thr Ser Glu Cys Asp Val Pro Glu Tyr Cys
     50                  55                  60

Asn Gly Ser Ser Gln Phe Cys Gln Pro Asp Val Phe
 65                  70                  75

<210> SEQ ID NO 23
<211> LENGTH: 76
<212> TYPE: PRT
<213> ORGANISM: Homo sapiens

<400> SEQUENCE: 23

Glu Met Gly Glu Asp Cys Asp Cys Gly Thr Ser Glu Glu Cys Thr Asn
 1               5                  10                  15

Ile Cys Cys Asp Ala Lys Thr Cys Lys Ile Lys Ala Thr Phe Gln Cys
                20                  25                  30

Ala Leu Gly Glu Cys Cys Glu Lys Cys Gln Phe Lys Lys Ala Gly Met
             35                  40                  45

Val Cys Arg Pro Ala Lys Asp Glu Cys Asp Leu Pro Glu Met Cys Asn
     50                  55                  60

Gly Lys Ser Gly Asn Cys Pro Asp Asp Arg Phe Gln
 65                  70                  75

<210> SEQ ID NO 24
<211> LENGTH: 76
<212> TYPE: PRT
<213> ORGANISM: Homo sapiens

<400> SEQUENCE: 24

Glu Arg Gly Glu Gln Cys Asp Cys Gly Pro Glu Asp Cys Arg Asn
 1               5                  10                  15

Arg Cys Cys Asn Ser Thr Thr Cys Gln Leu Ala Glu Gly Ala Gln Cys
                20                  25                  30

Ala His Gly Thr Cys Cys Gln Glu Cys Lys Val Lys Pro Ala Gly Glu
             35                  40                  45

Leu Cys Arg Pro Lys Lys Asp Met Cys Asp Leu Glu Glu Phe Cys Asp
     50                  55                  60

Gly Arg His Pro Glu Cys Pro Glu Asp Ala Phe Gln
 65                  70                  75

<210> SEQ ID NO 25
<211> LENGTH: 75
<212> TYPE: PRT
<213> ORGANISM: Homo sapiens

<400> SEQUENCE: 25

Glu Pro Gly Glu Gln Cys Asp Cys Gly Phe Leu Asp Asp Cys Val Asp
 1               5                  10                  15

Pro Cys Cys Asp Ser Leu Thr Cys Gln Leu Arg Pro Gly Ala Gln Cys
                20                  25                  30

Ala Ser Asp Gly Pro Cys Cys Gln Asn Cys Gln Leu Arg Pro Ser Gly
             35                  40                  45

Trp Gln Cys Arg Pro Thr Arg Gly Asp Cys Asp Leu Pro Glu Phe Cys
     50                  55                  60

Pro Gly Asp Ser Ser Gln Cys Pro Pro Asp Val
 65                  70                  75
```

```
<210> SEQ ID NO 26
<211> LENGTH: 61
<212> TYPE: PRT
<213> ORGANISM: Homo sapiens

<400> SEQUENCE: 26

Asn Arg Cys Cys Asn Ala Thr Thr Cys Thr Leu Lys Pro Asp Ala Val
1               5                   10                  15

Cys Ala His Gly Leu Cys Cys Glu Asp Cys Gln Leu Lys Pro Ala Gly
                20                  25                  30

Thr Ala Cys Arg Asp Ser Ser Asn Ser Cys Asp Leu Pro Glu Phe Cys
            35                  40                  45

Thr Gly Ala Ser Pro His Cys Pro Ala Asn Val Tyr Leu
        50                  55                  60

<210> SEQ ID NO 27
<211> LENGTH: 62
<212> TYPE: PRT
<213> ORGANISM: Homo sapiens

<400> SEQUENCE: 27

Asn Asn Pro Cys Cys Asn Ala Ser Asn Cys Thr Leu Arg Pro Gly Ala
1               5                   10                  15

Glu Cys Ala His Gly Ser Cys Cys His Gln Cys Lys Leu Leu Ala Pro
                20                  25                  30

Gly Thr Leu Cys Arg Glu Gln Ala Arg Gln Cys Asp Leu Pro Glu Phe
            35                  40                  45

Cys Thr Gly Lys Ser Pro His Cys Pro Thr Asn Phe Tyr Gln
        50                  55                  60

<210> SEQ ID NO 28
<211> LENGTH: 76
<212> TYPE: PRT
<213> ORGANISM: Homo sapiens

<400> SEQUENCE: 28

Glu Ala Gly Glu Glu Cys Asp Cys Gly Pro Gly Gln Glu Cys Arg Asp
1               5                   10                  15

Leu Cys Cys Phe Ala His Asn Cys Ser Leu Arg Pro Gly Ala Gln Cys
                20                  25                  30

Ala His Gly Asp Cys Cys Val Arg Cys Leu Leu Lys Pro Ala Gly Ala
            35                  40                  45

Leu Cys Arg Gln Ala Met Gly Asp Cys Asp Leu Pro Glu Phe Cys Thr
        50                  55                  60

Gly Thr Ser Ser His Cys Pro Pro Asp Val Tyr Leu
65                  70                  75

<210> SEQ ID NO 29
<211> LENGTH: 84
<212> TYPE: PRT
<213> ORGANISM: Homo sapiens

<400> SEQUENCE: 29

Glu Gln Gly Glu Glu Cys Asp Cys Gly Tyr Ser Asp Gln Cys Lys Asp
1               5                   10                  15

Glu Cys Cys Phe Asp Ala Asn Gln Pro Glu Gly Arg Lys Cys Lys Leu
                20                  25                  30

Lys Pro Gly Lys Gln Cys Ser Pro Ser Gln Gly Pro Cys Cys Thr Ala
            35                  40                  45
```

```
Gln Cys Ala Phe Lys Ser Lys Ser Glu Lys Cys Arg Asp Asp Ser Asp
         50                  55                  60

Cys Ala Arg Glu Gly Ile Cys Asn Gly Phe Thr Ala Leu Cys Pro Ala
 65                  70                  75                  80

Ser Asp Pro Lys

<210> SEQ ID NO 30
<211> LENGTH: 75
<212> TYPE: PRT
<213> ORGANISM: Homo sapiens

<400> SEQUENCE: 30

Asp Glu Gly Glu Cys Asp Pro Gly Ile Met Tyr Leu Asn Asn Asp
  1               5                  10                  15

Thr Cys Cys Asn Ser Asp Cys Thr Leu Lys Glu Gly Val Gln Cys Ser
             20                  25                  30

Asp Arg Asn Ser Pro Cys Cys Lys Asn Cys Gln Phe Glu Thr Ala Gln
         35                  40                  45

Lys Lys Cys Gln Glu Ala Ile Asn Ala Thr Cys Lys Gly Val Ser Tyr
 50                  55                  60

Cys Thr Gly Asn Ser Ser Glu Cys Pro Pro Pro
 65                  70                  75

<210> SEQ ID NO 31
<211> LENGTH: 76
<212> TYPE: PRT
<213> ORGANISM: Mus musculus

<400> SEQUENCE: 31

Glu His Gly Glu Gln Cys Asp Cys Gly Thr Pro Gln Asp Cys Gln Asn
  1               5                  10                  15

Pro Cys Cys Asn Ala Thr Thr Cys Gln Leu Val Lys Gly Ala Glu Cys
             20                  25                  30

Ala Ser Gly Thr Cys Cys His Glu Cys Lys Val Lys Pro Ala Gly Glu
         35                  40                  45

Val Cys Arg Leu Ser Lys Asp Lys Cys Asp Leu Glu Glu Phe Cys Asp
 50                  55                  60

Gly Arg Lys Pro Thr Cys Pro Glu Asp Ala Phe Gln
 65                  70                  75

<210> SEQ ID NO 32
<211> LENGTH: 76
<212> TYPE: PRT
<213> ORGANISM: Mus musculus

<400> SEQUENCE: 32

Glu Met Asn Glu Asp Cys Asp Cys Gly Thr Pro Lys Glu Cys Thr Asn
  1               5                  10                  15

Lys Cys Cys Asp Ala Arg Thr Cys Lys Ile Lys Ala Gly Phe Gln Cys
             20                  25                  30

Ala Leu Gly Glu Cys Cys Glu Cys Gln Leu Lys Pro Gly Val
         35                  40                  45

Val Cys Arg Ala Ala Lys Asp Glu Cys Asp Leu Pro Glu Val Cys Asp
 50                  55                  60

Gly Lys Ser Ser His Cys Pro Gly Asp Arg Phe Arg
 65                  70                  75
```

```
<210> SEQ ID NO 33
<211> LENGTH: 61
<212> TYPE: PRT
<213> ORGANISM: Mus musculus

<400> SEQUENCE: 33

Asn Arg Cys Cys Asn Ala Thr Thr Cys Thr Leu Lys Pro Asp Ala Val
1               5                   10                  15

Cys Ala His Gly Gln Cys Cys Glu Asp Cys Gln Leu Lys Pro Pro Gly
                20                  25                  30

Thr Ala Cys Arg Gly Ser Ser Asn Ser Cys Asp Leu Pro Glu Phe Cys
            35                  40                  45

Thr Gly Thr Ala Pro His Cys Pro Ala Asn Val Tyr Leu
        50                  55                  60

<210> SEQ ID NO 34
<211> LENGTH: 61
<212> TYPE: PRT
<213> ORGANISM: Mus musculus

<400> SEQUENCE: 34

Lys Asn Pro Cys Cys Asn Ala Ser Asn Cys Thr Leu Lys Glu Gly Ala
1               5                   10                  15

Glu Cys Ala His Gly Ser Cys Cys His Gln Cys Lys Leu Val Ala Pro
                20                  25                  30

Gly Thr Gln Cys Arg Glu Gln Val Arg Gln Cys Asp Leu Pro Glu Phe
            35                  40                  45

Cys Thr Gly Lys Ser Pro His Cys Pro Thr Asn Tyr Tyr
        50                  55                  60

<210> SEQ ID NO 35
<211> LENGTH: 76
<212> TYPE: PRT
<213> ORGANISM: Mus musculus

<400> SEQUENCE: 35

Glu Ala Gly Glu Glu Cys Asp Cys Gly Ser Gly Gln Lys Cys Pro Asp
1               5                   10                  15

Pro Cys Cys Phe Ala His Asn Cys Ser Leu Arg Ala Gly Ala Gln Cys
                20                  25                  30

Ala His Gly Asp Cys Cys Ala Arg Cys Leu Leu Lys Ser Ala Gly Thr
            35                  40                  45

Pro Cys Arg Pro Ala Ala Thr Asp Cys Asp Leu Pro Glu Phe Cys Thr
        50                  55                  60

Gly Thr Ser Pro Tyr Cys Pro Ala Asp Val Tyr Leu
65                  70                  75

<210> SEQ ID NO 36
<211> LENGTH: 75
<212> TYPE: PRT
<213> ORGANISM: Mus musculus

<400> SEQUENCE: 36

Asp Pro Gly Glu Gln Cys Asp Cys Gly Phe Pro Asp Glu Cys Thr Asp
1               5                   10                  15

Pro Cys Cys Asp His Phe Thr Cys Gln Leu Arg Pro Gly Ala Gln Cys
                20                  25                  30

Ala Ser Asp Gly Pro Cys Cys Gln Asn Cys Lys Leu His Pro Ala Gly
            35                  40                  45
```

```
Trp Leu Cys Arg Pro Pro Thr Asp Asp Cys Asp Leu Pro Glu Phe Cys
 50                  55                  60
Pro Gly Asp Ser Ser Gln Cys Pro Ser Asp Ile
 65                  70                  75
```

<210> SEQ ID NO 37
<211> LENGTH: 76
<212> TYPE: PRT
<213> ORGANISM: Mus musculus

<400> SEQUENCE: 37

```
Asp Pro Gly Glu Glu Cys Asp Cys Gly Thr Ala Lys Glu Cys Glu Val
 1               5                   10                  15
Asp Pro Cys Cys Glu Gly Ser Thr Cys Lys Leu Lys Ser Phe Ala Glu
                20                  25                  30
Cys Ala Tyr Gly Asp Cys Cys Lys Asp Cys Gln Phe Leu Pro Gly Gly
            35                  40                  45
Ser Met Cys Arg Gly Lys Thr Ser Glu Cys Asp Val Pro Glu Tyr Cys
 50                  55                  60
Asn Gly Ser Ser Gln Phe Cys Pro Pro Asp Val Phe
 65                  70                  75
```

<210> SEQ ID NO 38
<211> LENGTH: 84
<212> TYPE: PRT
<213> ORGANISM: Mus musculus

<400> SEQUENCE: 38

```
Glu Gln Gly Glu Glu Cys Asp Cys Gly Tyr Ser Asp Gln Cys Lys Asp
 1               5                   10                  15
Asp Cys Cys Phe Asp Ala Asn Gln Pro Glu Gly Lys Lys Cys Lys Leu
                20                  25                  30
Lys Pro Gly Lys Gln Cys Ser Pro Ser Gln Gly Pro Cys Cys Thr Ala
            35                  40                  45
Gln Cys Ala Phe Lys Ser Lys Ser Glu Lys Cys Arg Asp Asp Ser Asp
 50                  55                  60
Cys Ala Lys Glu Gly Ile Cys Asn Gly Phe Thr Ala Leu Cys Pro Ala
 65                  70                  75                  80
Ser Asp Pro Lys
```

<210> SEQ ID NO 39
<211> LENGTH: 75
<212> TYPE: PRT
<213> ORGANISM: Mus musculus

<400> SEQUENCE: 39

```
Asp Glu Gly Glu Glu Cys Asp Pro Gly Ile Met Tyr Leu Asn Asn Asp
 1               5                   10                  15
Thr Cys Cys Asn Ser Asp Cys Thr Leu Lys Pro Gly Val Gln Cys Ser
                20                  25                  30
Asp Arg Asn Ser Pro Cys Cys Lys Asn Cys Gln Phe Glu Thr Ala Gln
            35                  40                  45
Lys Lys Cys Gln Glu Ala Ile Asn Ala Thr Cys Lys Gly Val Ser Tyr
 50                  55                  60
Cys Thr Gly Asn Ser Ser Glu Cys Pro Pro Pro
 65                  70                  75
```

```
<210> SEQ ID NO 40
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Lys

<400> SEQUENCE: 40

Arg Gly Lys Thr Ser Glu
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ala

<400> SEQUENCE: 41

Arg Pro Ala Lys Asp Glu
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (2)..(2)
<223> OTHER INFORMATION: beta-Lys

<400> SEQUENCE: 42

Arg Pro Lys Lys Asp Met
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
```

```
<220> FEATURE:
<221> NAME/KEY: MOD_RES
<222> LOCATION: (3)..(3)
<223> OTHER INFORMATION: beta-Thr

<400> SEQUENCE: 43

Arg Pro Thr Arg Gly Asp
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ser

<400> SEQUENCE: 44

Arg Asp Ser Ser Asn Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Gln

<400> SEQUENCE: 45

Arg Glu Gln Ala Arg Gln
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ala

<400> SEQUENCE: 46

Arg Gln Ala Met Gly Asp
1               5
```

```
<210> SEQ ID NO 47
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Synthetic peptide is cyclic with terminal amino
      acids joined
<220> FEATURE:
<221> NAME/KEY: MOD_RES
<222> LOCATION: (2)..(2)
<223> OTHER INFORMATION: beta-Asp

<400> SEQUENCE: 47

Arg Asp Asp Ser Asp
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: Synthetic peptide is cyclic with terminal amino
      acids joined
<220> FEATURE:
<221> NAME/KEY: MOD_RES
<222> LOCATION: (4)..(4)
<223> OTHER INFORMATION: beta-Ile

<400> SEQUENCE: 48

Gln Glu Ala Ile Asn Ala Thr
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ser

<400> SEQUENCE: 49

Arg Leu Ser Lys Asp Lys
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
```

```
<220> FEATURE:
<221> NAME/KEY: MOD_RES
<222> LOCATION: (3)..(3)
<223> OTHER INFORMATION: beta-Ala

<400> SEQUENCE: 50

Arg Ala Ala Lys Asp Glu
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ser

<400> SEQUENCE: 51

Arg Gly Ser Ser Asn Ser
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Gln

<400> SEQUENCE: 52

Arg Glu Gln Val Arg Gln
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ala

<400> SEQUENCE: 53

Arg Pro Ala Ala Thr Asp
1               5
```

-continued

```
<210> SEQ ID NO 54
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Pro

<400> SEQUENCE: 54

Arg Pro Pro Thr Asp Asp
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Xaa is homophenylalanine

<400> SEQUENCE: 55

Leu Ala Gln Ala Xaa Arg Ser Cys
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (1)..(1)
<223> OTHER INFORMATION: beta-Arg

<400> SEQUENCE: 56

Arg Leu Ser Lys Asp Lys
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (2)..(2)
<223> OTHER INFORMATION: beta-Leu
```

```
<400> SEQUENCE: 57

Arg Leu Ser Lys Asp Lys
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ser

<400> SEQUENCE: 58

Arg Leu Ser Ala Asp Lys
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ser

<400> SEQUENCE: 59

Arg Leu Ser Lys Ala Lys
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Synthetic peptide is cyclic with terminal amino
      acids joined
<220> FEATURE:
<221> NAME/KEY: MOD_RES
<222> LOCATION: (3)..(3)
<223> OTHER INFORMATION: beta-Ser

<400> SEQUENCE: 60

Arg Leu Ser Lys Asp Ala
1               5

<210> SEQ ID NO 61
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 61

Leu Ala Gln Ala
1
```